(12) United States Patent
Roberts et al.

(10) Patent No.: US 9,376,833 B2
(45) Date of Patent: Jun. 28, 2016

(54) DOOR HANDLE

(75) Inventors: Matthew Geoffrey Roberts, Hampshire (GB); Alan Michael George Meeks, Chichester (GB)

(73) Assignee: PURE HOLD LIMITED, Waterlooville, Hampshire (GB)

( * ) Notice: Subject to any disclaimer, the term of this patent is extended or adjusted under 35 U.S.C. 154(b) by 861 days.

(21) Appl. No.: 13/641,067

(22) PCT Filed: Apr. 15, 2011

(86) PCT No.: PCT/GB2011/000590
§ 371 (c)(1),
(2), (4) Date: Jul. 9, 2013

(87) PCT Pub. No.: WO2011/128652
PCT Pub. Date: Oct. 20, 2011

(65) Prior Publication Data
US 2013/0279966 A1  Oct. 24, 2013

(30) Foreign Application Priority Data

Apr. 16, 2010 (GB) .................................. 1006366.7

(51) Int. Cl.
  *E05B 1/00* (2006.01)
  *A61L 2/10* (2006.01)
  *A61L 2/18* (2006.01)
  *E05B 63/00* (2006.01)

(52) U.S. Cl.
  CPC ................. *E05B 1/0069* (2013.01); *A61L 2/10* (2013.01); *A61L 2/18* (2013.01); *E05B 63/0056* (2013.01); *Y10T 16/444* (2015.01)

(58) Field of Classification Search
  CPC combination set(s) only.
  See application file for complete search history.

(56) References Cited

U.S. PATENT DOCUMENTS

| 6,211,788 B1* | 4/2001 | Lynn ................... A47K 13/105 15/1 |
| 6,942,408 B2* | 9/2005 | Smith ................... B43K 29/00 401/131 |
| 7,175,807 B1* | 2/2007 | Jones ................... E05B 1/0069 250/455.11 |
| 7,458,742 B2* | 12/2008 | Stropkay .................. A47K 5/12 401/133 |
| 2005/0011042 A1 | 1/2005 | Hupp et al. |

(Continued)

FOREIGN PATENT DOCUMENTS

| DE | 202004006845 | 8/2004 |
| EP | 1164235 | 1/2002 |

(Continued)

OTHER PUBLICATIONS

Office Action dated Sep. 2, 2014 in Japanese Patent Application No. 2013-504336, with English translation, 4 pages.

(Continued)

*Primary Examiner* — David Walczak
(74) *Attorney, Agent, or Firm* — Vierra Magen Marcus LLP

(57) ABSTRACT

A door handle (1) is adapted to apply liquid or gel (liquid/gel) to a user's hand. The handle (1) comprises a handle grip (2) and a liquid/gel reservoir (6) associated with the handle (1). A liquid/gel displacement device is arranged in the grip (2) and a non-return valve (53) is provided to allow liquid/gel to flow from the reservoir (6) to the displacement device. A hollow trigger (8) is displaceably mounted on the grip (2) and adapted to actuate the displacement device when the handle (1) is gripped for displacement of liquid/gel from the displacement device, into the trigger (8) and then on to a hand or its digits gripping the trigger (8).

10 Claims, 31 Drawing Sheets

(56) References Cited

U.S. PATENT DOCUMENTS

2006/0245818 A1 11/2006 Stropkay
2008/0305020 A1* 12/2008 Oshmyansky ............ A61L 2/18
  422/291

FOREIGN PATENT DOCUMENTS

| GB | 2421897 | 7/2006 |
| GB | 2436284 | 9/2007 |
| JP | 771143 | 3/1995 |
| WO | 2008153711 A1 | 12/2008 |
| WO | WO 2008/153711 | 12/2008 |

OTHER PUBLICATIONS

Machine Translation of JP 771143, published Mar. 14, 1995, 12 pages.

Notice of Allowance dated Jan. 30, 2016 in Australian Patent Application No. 2011239739.

* cited by examiner

DOOR HANDLE

This application is a U.S. national stage filing of International Application No. PCT/GB2011/000590, filed Apr. 15, 2011, which claims priority to GB1006366.7, filed Apr. 16, 2010, both which are incorporated herein by reference in its entirety.

BACKGROUND OF THE INVENTION

The present invention relates to a door handle adapted to apply liquid or gel to a user's hand.

Application of disinfectant gel to users' hands is recognised to improve cleanliness and control spread of infection, particularly in public buildings such as schools and hospitals. Typically self standing or wall mounted disinfectant sprays or pumps are fitted at door ways to allow a user to apply the disinfectant before entering a building or entering a room within the building. However, despite being instructed, not all users apply the disinfectant. Therefore, an alternative approach is needed.

A known approach is to provide a door handle that applies a disinfectant in the form of a liquid or gel to a user's hand. Known door handles for applying liquid or gel to a user's hand fall within two designs.

In the first design, a door handle is fitted with a pump arrangement, typically in the form of a piston [1, 2, 3]. The pump is in fluid communication with a reservoir containing the disinfectant liquid or gel. The pump is also coupled to the door handle and the door, such that the rotary action of the door handle being turned by a user to open the door actuates the pump. When the pump is actuated the disinfectant is applied to a surface of the door handle. A similar pump device has also been applied to a pull-handle [1]. The pull-handle is mounted to a door using mounting points that allow the handle to move with respect to the mounting points when the door handle is pulled to open the door. A pump arrangement is fitted within the door handle and coupled between the mounting points and the door handle. When the door is opened, the door handle moves with respect to its mounting points, such that the disinfectant is pumped from a reservoir coupled to the pump and onto a surface of the door handle.

In the second design, the door handle is provided with a grip that is provided with a disinfectant gel or liquid. The disinfectant gel or liquid may be supplied from a reservoir. When a user grips the door handle the disinfectant liquid or gel is applied to the user's hand. The grip may include a porous cover [4, 5, 6] or the handle may be provided with an absorbent material within a hollow grip, such that he absorbent martial is exposed through holes in the hollow grip [5, 7]. The grip may include a plastic shroud having a fluid outlet in the form of a flap, such that when the door handle is gripped the cover is deformed to open the flap [8].

The object of the present invention is to provide an improved disinfectant liquid or gel applying door handle.

SUMMARY OF THE INVENTION

According to the invention there is provided a door handle adapted to apply liquid or gel (liquid/gel) to a user's hand, the handle comprising:
 a handle grip,
 a liquid/gel reservoir associated with the handle,
 a liquid/gel displacement device in the grip,
 an optional non-return valve allowing liquid/gel flow from the reservoir to the displacement device,
 a hollow trigger displaceably mounted on the grip and adapted to actuate the displacement device when the handle is gripped for displacement of liquid/gel from the device, into the trigger and thence on to a hand or its digits gripping the trigger.

Although reservoir could be arranged in use below the displacement device, with the liquid/gel being sucked up from it, normally the use position of the reservoir will be above the grip with gravity assisting or causing the liquid/gel to flow down and.

Whilst it is envisaged that the displacement device could be a piston and cylinder device, or a diaphragm and chamber device, which devices would normally be expected to require a return spring for the cylinder or chamber and the trigger, preferably, the displacement device is a resilient device of elastomeric material adapted to return from its shape after displacement of liquid or gel to its original shape for replenishing the displacement device.

In accordance with a particular feature, the trigger is provided with a plurality of liquid/gel outlets which are normally closed and are individually opened by digital pressure on them, whereby the liquid or gel is expelled selectively where the digits act against the trigger.

In the prototype, individual balls are provided to close individual outlets, with each ball being urged into its outlet by a respective spring. The springs can be coil springs or leaf springs in the form of tabs bent from a single strip. For production, it is envisaged that the balls can be replaced by closure members integrally moulded to resilient fingers, which urge their closure members into the outlets.

The door handle may comprise a second grip adapted to provide a physical antibacterial action to compliment the liquid/gel of the first grip which provides a chemical antibacterial action.

The door handle may comprise a guard member arranged to protect the reservoir from impact, if a door on which the handle is mounted is opened and brought into contact with an adjacent wall.

The door handle may comprise a second, upper liquid/gel reservoir removably mounted on the handle which, when fitted, is in fluid communication with the lower liquid/gel reservoir by virtue of an aperture of the upper liquid/gel reservoir engaging with an aperture of the lower liquid/gel reservoir.

According to an embodiment of the invention there is provided a door handle comprising: a first grip adapted to provide a chemical antibacterial action by applying liquid or gel (liquid/gel) to a user's hand; and a second grip adapted to provide a physical antibacterial action.

The second grip may have a surface made of a material with an antibacterial action, or the second grip may incorporate an ultraviolet (UV) light source adapted to radiate UV light from inside the second grip to a UV-transparent outer surface of the grip, thereby providing an antibacterial action.

The first grip may extend vertically and the second grip may extend vertically and the second grip may be arranged below and in line with the first grip.

According to an embodiment of the invention there is provided a door handle comprising: a grip adapted to apply liquid or gel (liquid/gel) to a user's hand; a liquid/gel reservoir in fluid communication with the grip; and a guard member arranged to protect the reservoir from impact, if a door to which the handle is fitted is opened and brought into contact with an adjacent wall.

According to an embodiment of the invention there is provided a grip adapted to apply liquid or gel (liquid/gel) to a user's hand; a first, lower liquid/gel reservoir in fluid communication with the grip; and a second, upper liquid/gel reservoir removably mounted on the handle which, when fitted, is in fluid communication with the lower liquid/gel reservoir by virtue of an aperture of the upper liquid/gel reservoir engaging with an aperture of the lower liquid/gel reservoir.

The lower liquid/gel reservoir may have a flap that is arranged to be movable between a closed position and an open position, wherein absent actuation and when the upper liquid/gel reservoir is not fitted the flap adopts the closed position in which the flap forms a closure over the aperture in the lower liquid/gel reservoir and wherein fitment of the upper liquid/gel reservoir to the handle urges the flap into its open position which allows liquid/gel transfer from the upper liquid/gel reservoir to the lower liquid/gel reservoir.

The lower liquid/gel reservoir may comprise a vent element arranged in an upper surface portion thereof, which is connected to the flap, such that when the flap is in the closed position the vent is closed and when the flap is in the open position the vent is open to facilitate filling of the lower liquid/gel reservoir with liquid/gel from the upper liquid/gel reservoir.

The lower liquid/gel reservoir may have an integral visual level indicator or may comprise a light arranged to illuminate at least one of the upper and lower liquid/gel reservoirs and a switch arranged to be actuated by fitment of the upper liquid/gel reservoir and thereby turn on the light.

According to an embodiment of the invention there is provided a door handle adapted to apply liquid or gel (liquid/gel) to a user's hand, the handle comprising: a liquid/gel reservoir; a grip in fluid communication with the liquid/gel reservoir; a liquid/gel displacement device disposed in the grip; and a trigger comprising a liquid/gel outlet, wherein the trigger is displacably mounted on the grip and adapted to actuate the displacement device when the handle is gripped for displacement of liquid/gel from liquid/gel outlet and onto a surface of the trigger.

According to an embodiment of the invention there is provided a door to which is fitted a door handle according to any of the above door handles. If the door handle comprises a first and second grip, the first grip may be arranged at an optimum height for door actuation by an adult so that the second grip is lower, thereby through ergonomics making it more likely that a user will open the door using the first grip.

BRIEF DESCRIPTION OF THE DRAWINGS

The invention is now described by way of example only with reference to the following drawings in which.

DETAILED DESCRIPTION

FIGS. 1 to 16 illustrate a door handle according to a first embodiment of the invention.

Figure 1:
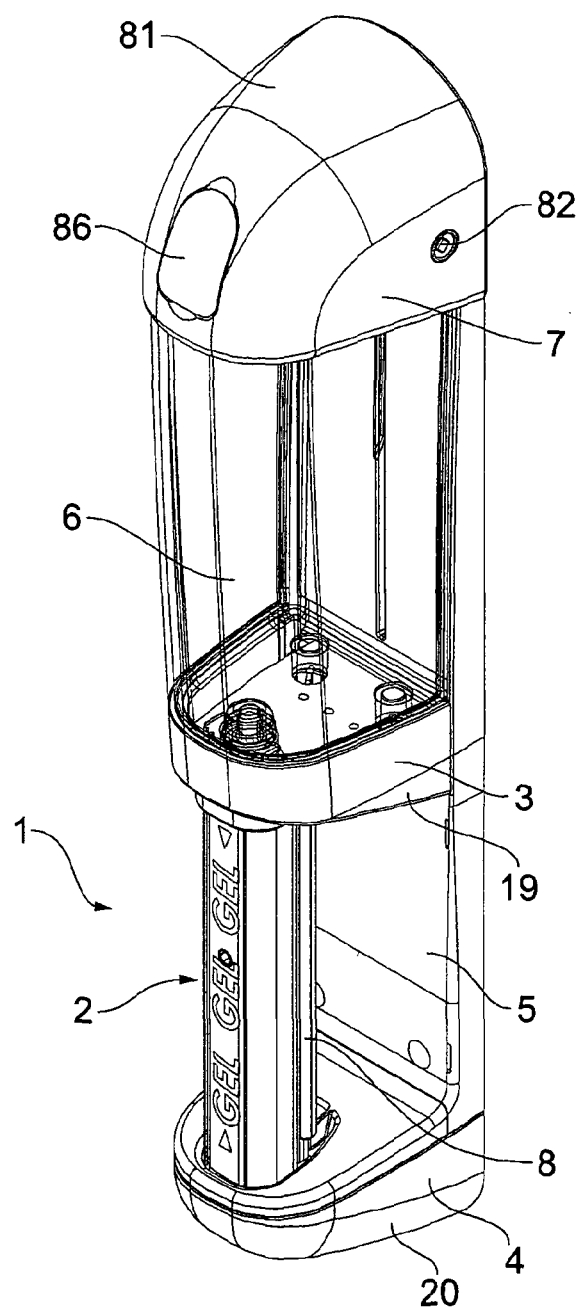
FIG. 1 is a perspective view of a door handle in accordance with a first embodiment of the invention.
Figure 2:
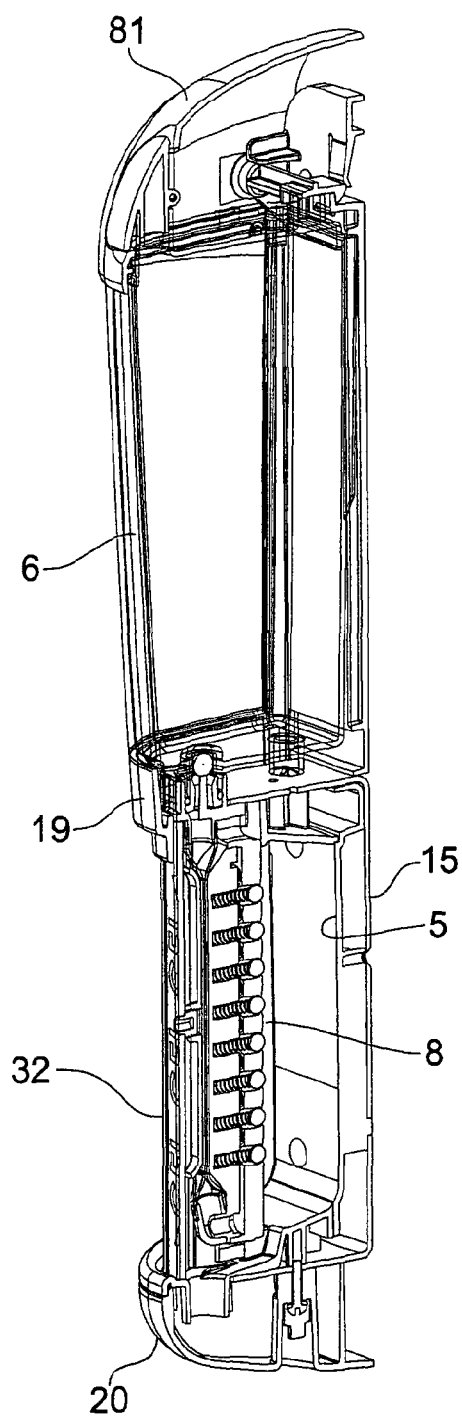
FIG. 2 is a similar perspective view of the door handle of FIG. 1, sectioned on a central vertical plane.
Figure 3:
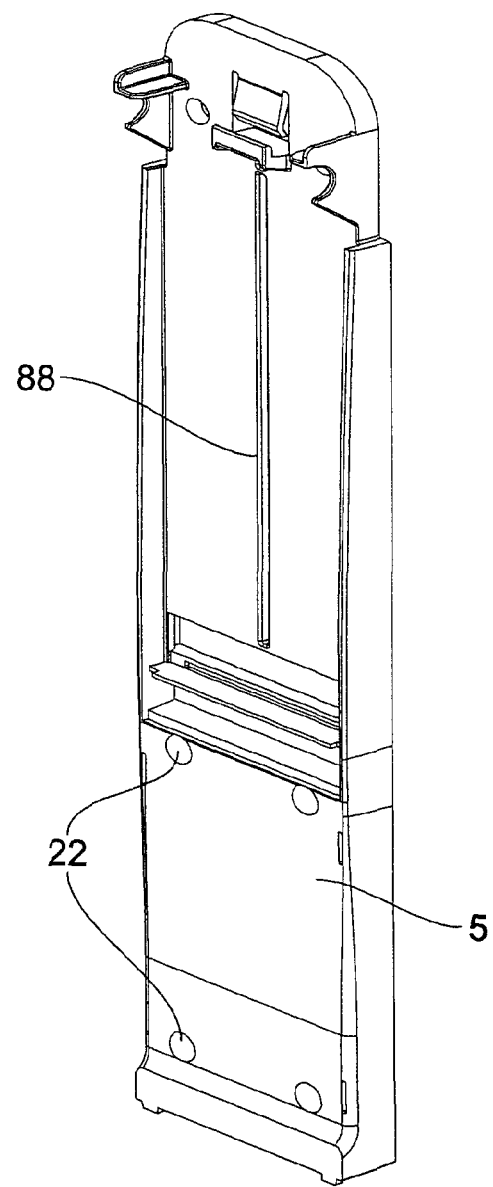
FIG. 3 is a perspective view of a door plate of the door handle.
Figure 4:
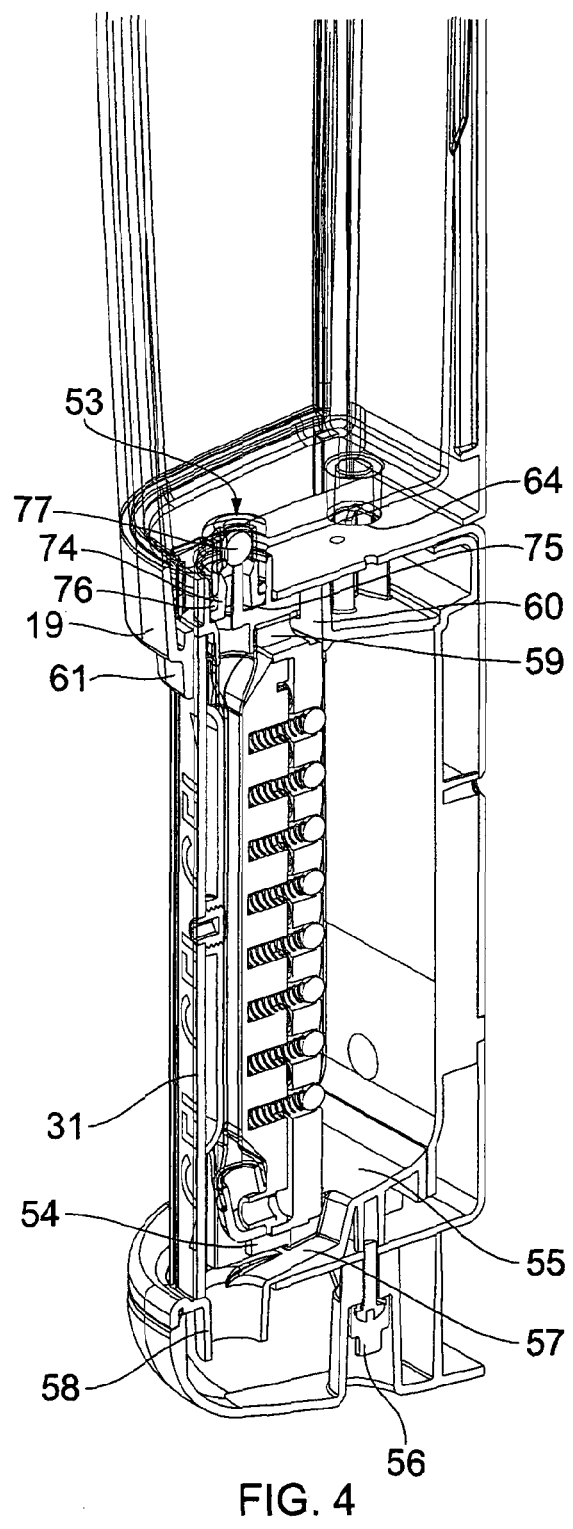
FIG. 4 is a view similar to FIG. 2 on a larger scale.
Figure 5:
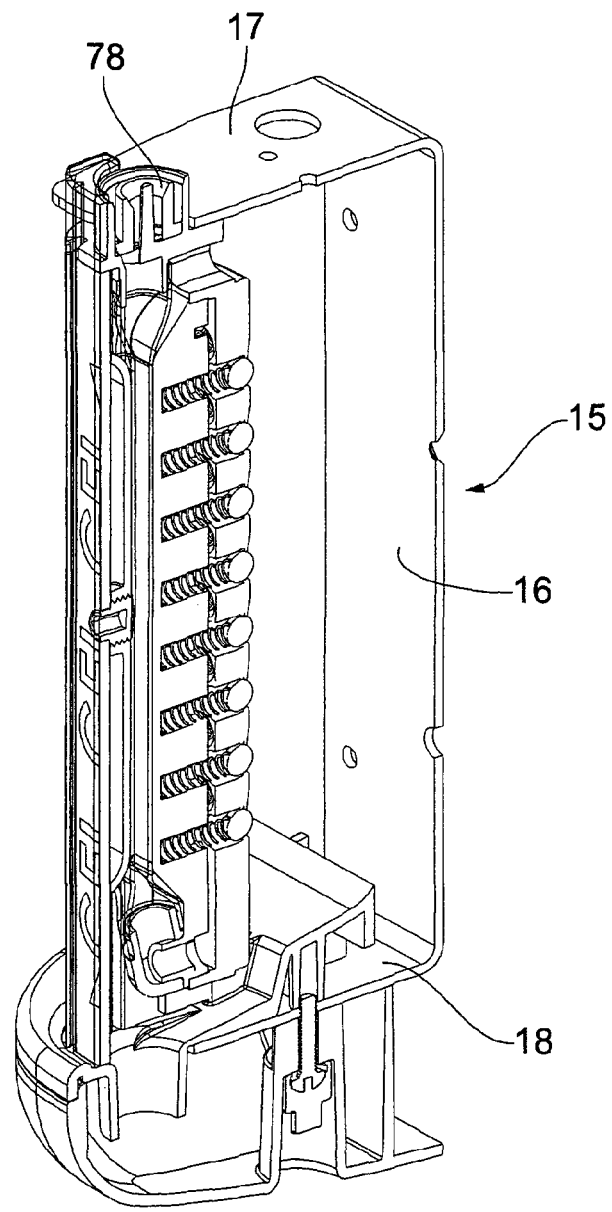
FIG. 5 is a view similar to FIG. 4 with many components removed to show a metal pressing supporting a grip of the handle.
Figure 6:
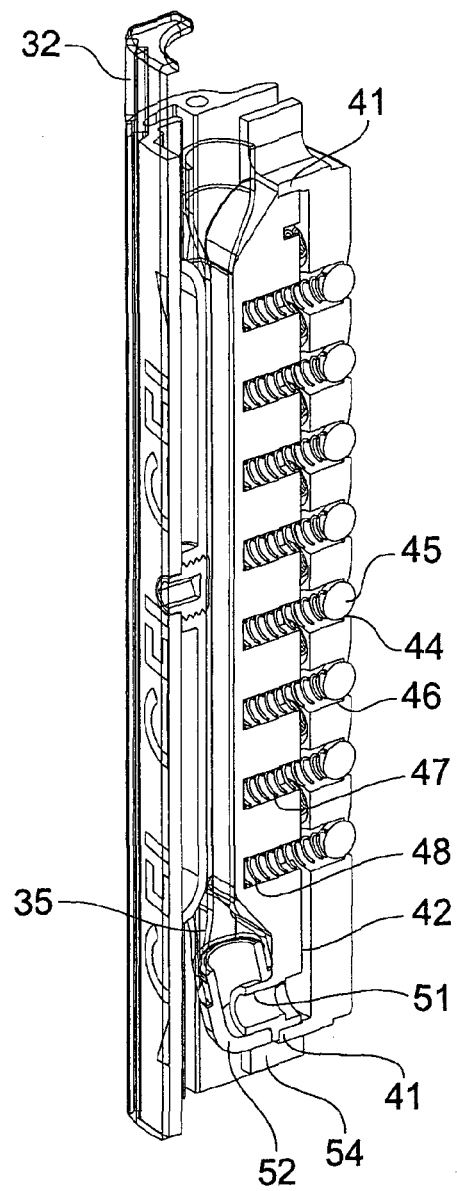
FIG. 6 is a similar view of the grip only.
Figure 7:
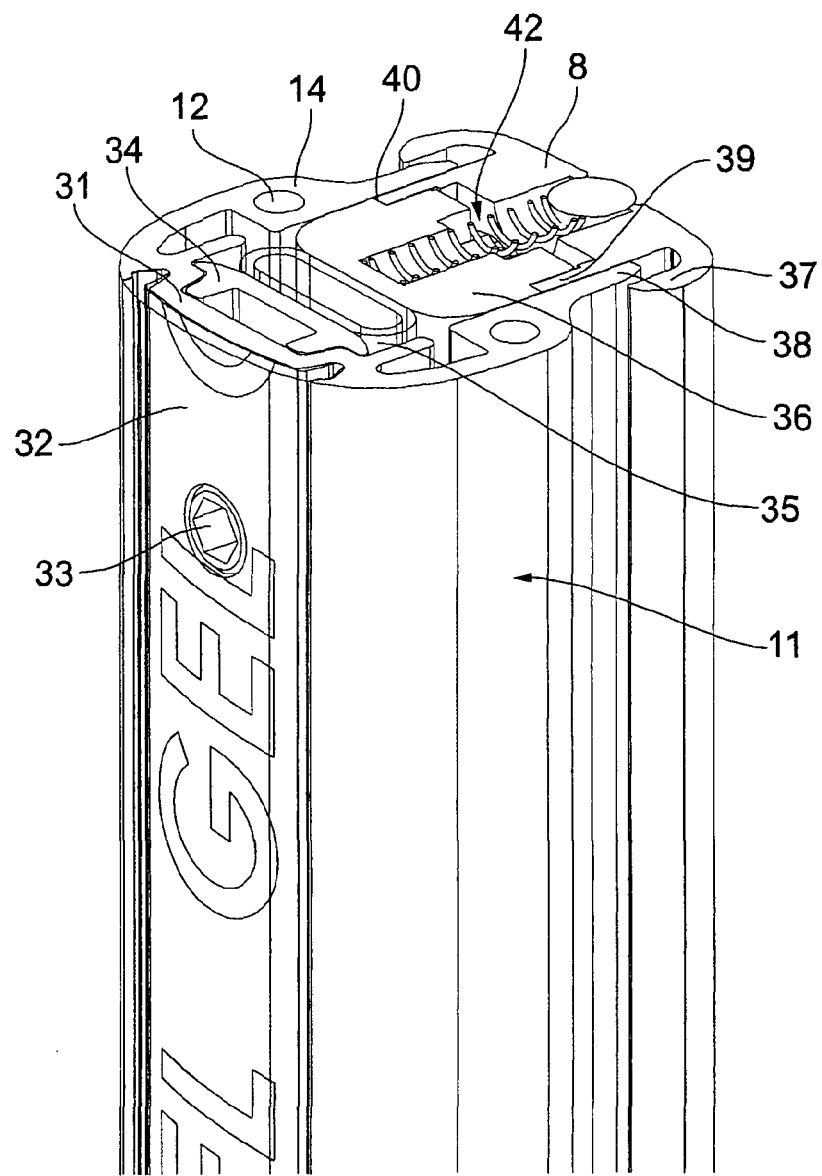
FIG. 7 is a horizontal section through the grip.
Figure 8:
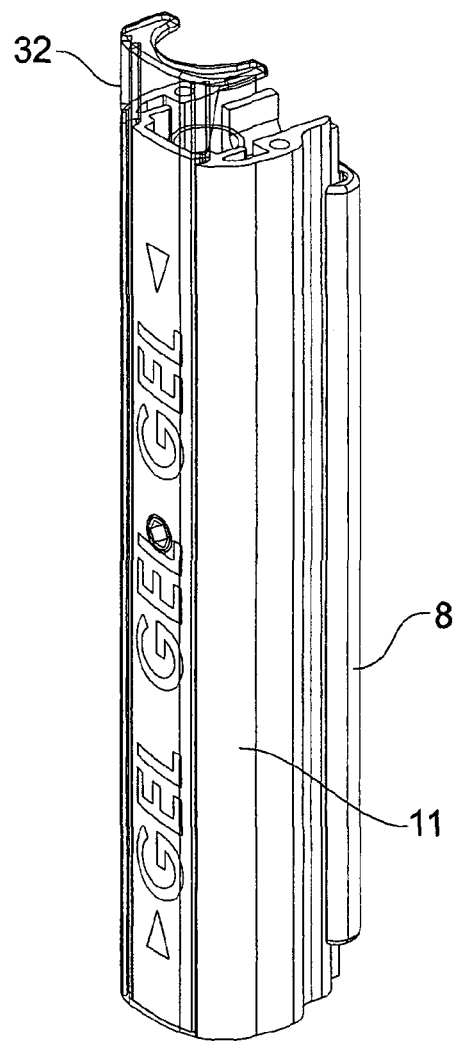
FIG. 8 is a non-sectioned view similar to FIG. 6.
Figure 9:
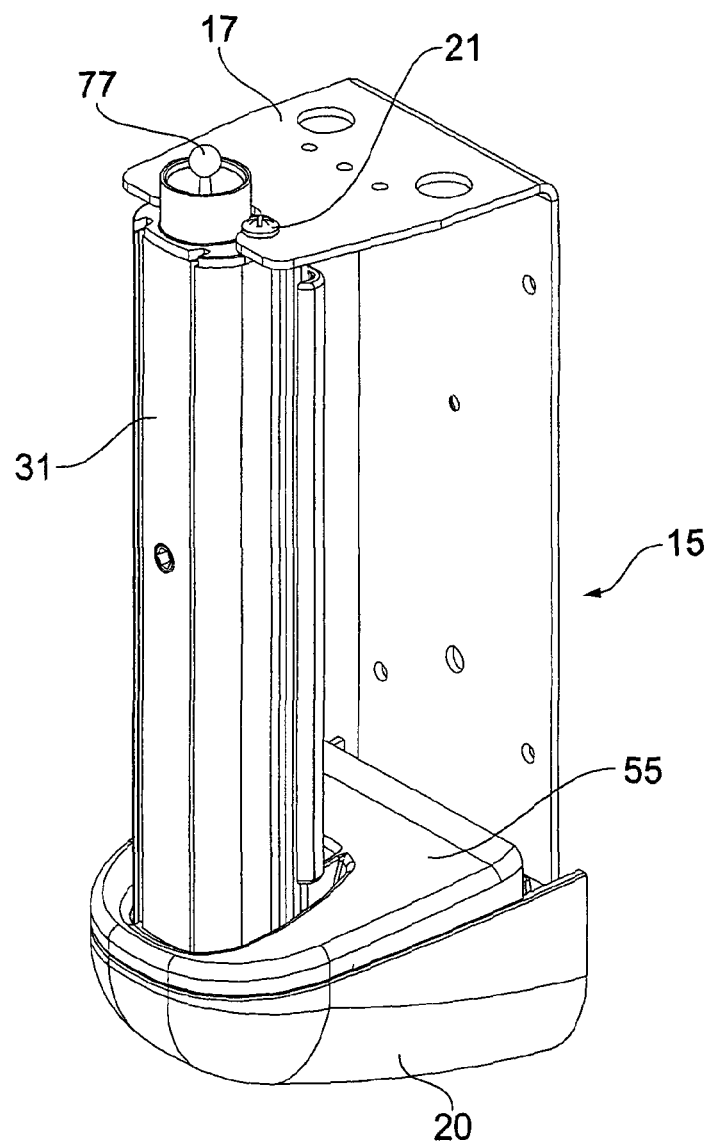
FIG. 9 is a non-sectioned view similar to FIG. 5.
Figure 10:
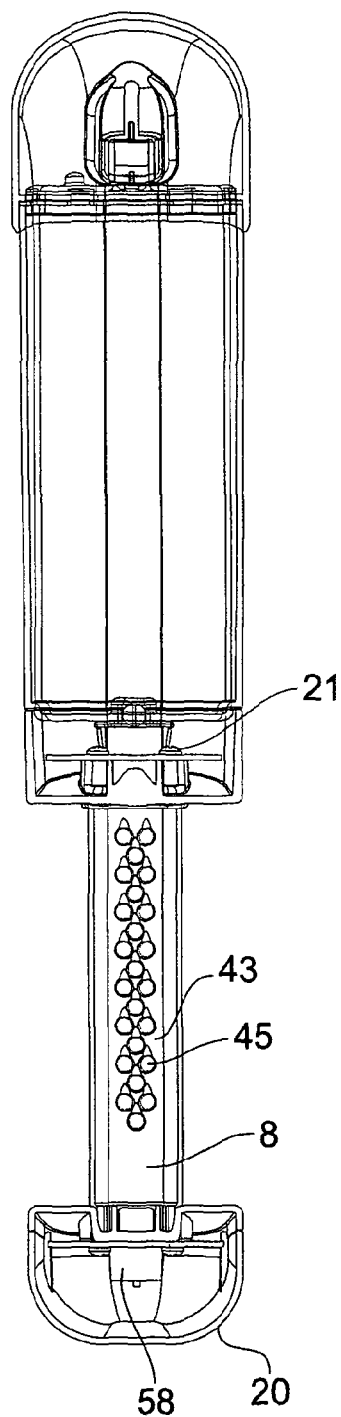
FIG. 10 is a sectional view from the direction of the door on a plane parallel with the door.
Figure 11:
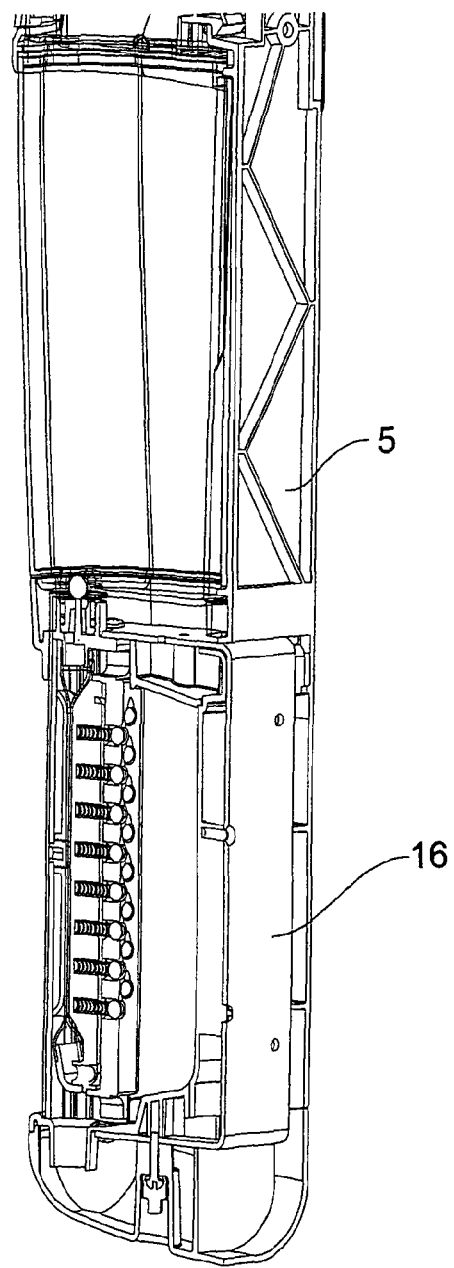
FIG. 11 is a sectional view on the plane of FIG. 2 in perspective from the door.
Figure 12:
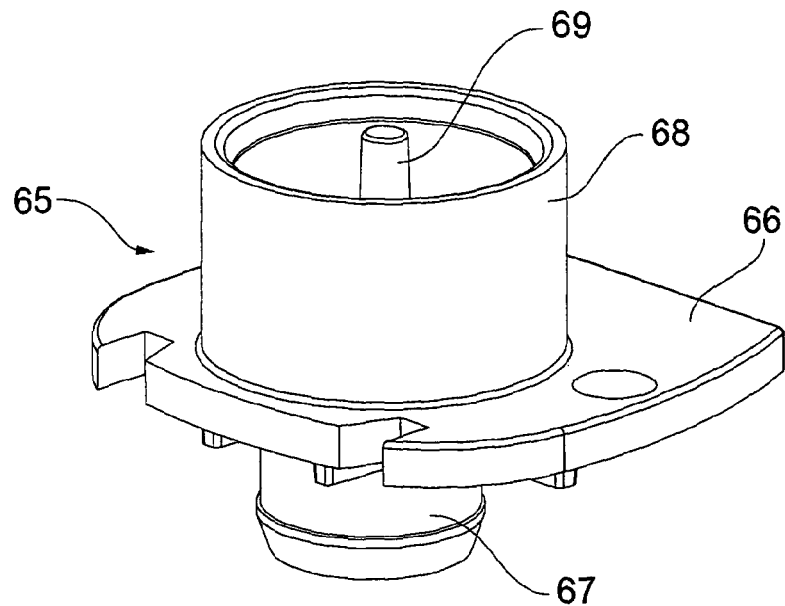
FIG. 12 is a perspective view of a reservoir to displacement vessel adapter.
Figure 13:
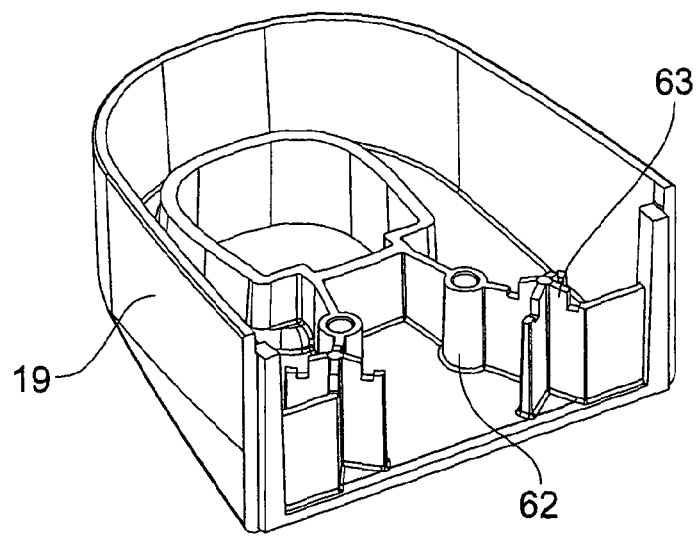
FIG. 13 is a perspective view of an upper moulding for locating the trigger.
Figure 14:
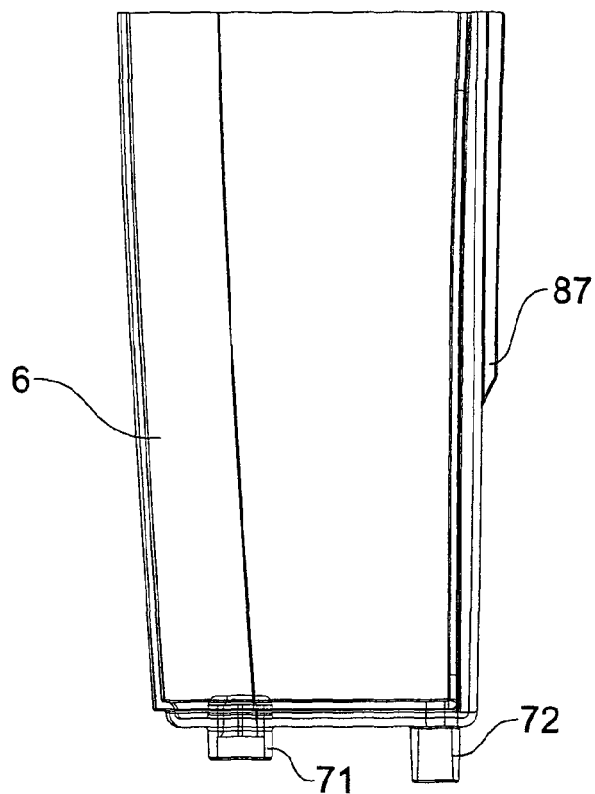
FIG. 14 is a side view of a reservoir of the handle.
Figure 15:
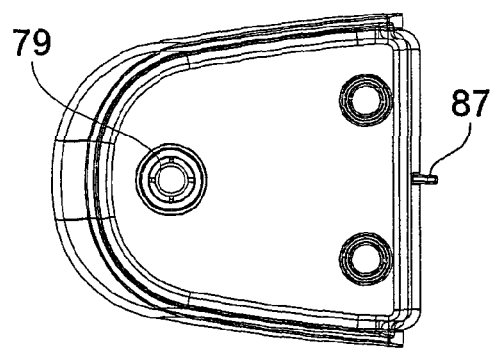
FIG. 15 is a plan view of the reservoir.
Figure 16:
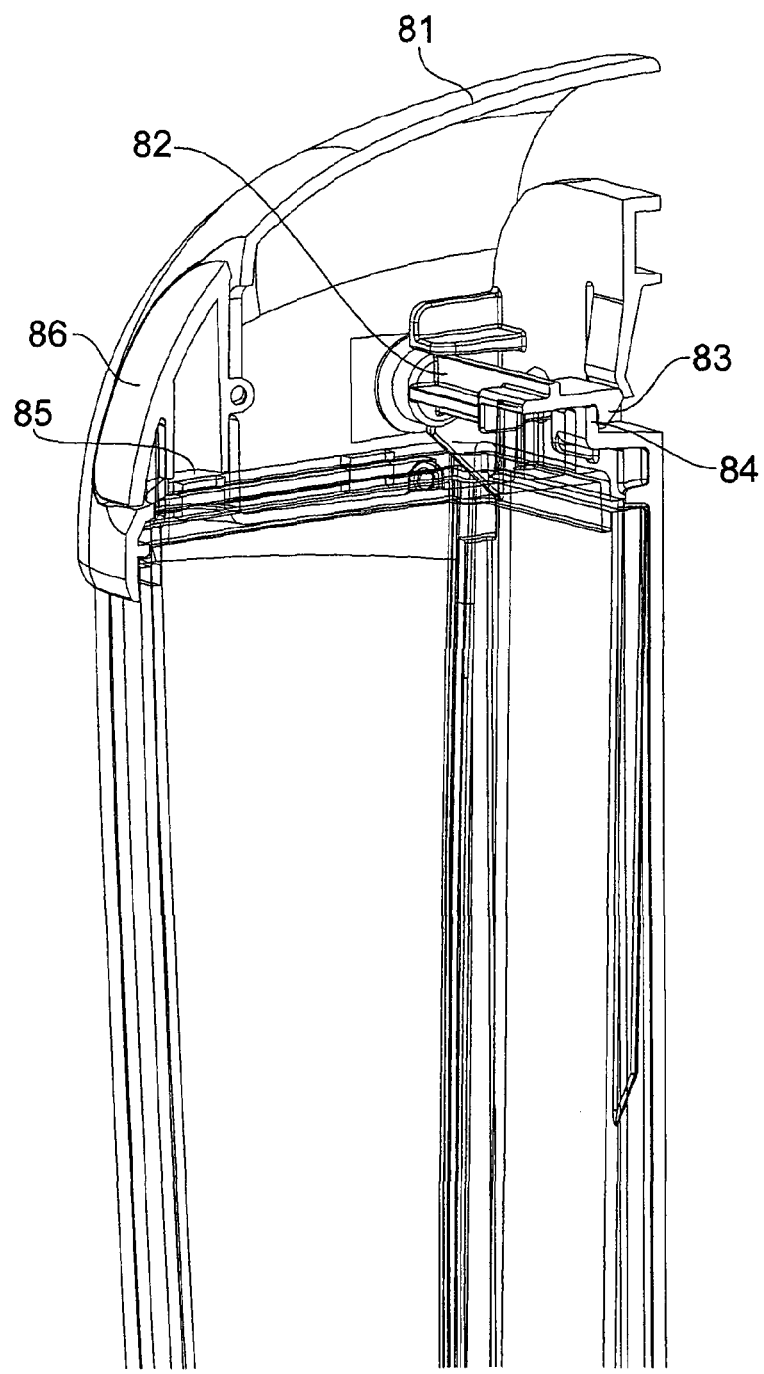
FIG. 16 is a sectional perspective view showing the top of the reservoir.

Referring first to FIG. 1 of the drawings, a door handle 1 has a grip 2 connected via two brackets 3, 4 to a door plate 5 fast in use with a door (not shown). Above the grip is arranged a disinfectant gel reservoir 6. The door plate 5 extends up to a further bracket 7. A trigger 8 on the door side of the grip is displaceable towards the grip to dispense disinfectant gel from reservoir onto digits of a hand pulling on the grip.

The description of FIGS. 1 to 16 will describe in sequence:
the structural arrangement of the grip;
the gel displacement arrangements; and then
the ancillary details.

There are numerous Figures (FIGS. 1 to 16) in the drawings, which are CAD drawings, with views chosen to illustrate particular features. It is suggested that if a feature cannot be found quickly in one Figure, the others should be referred to.

The grip 2 is based on an extrusion 11, having two bores 12 in its sidewalls 14. It is fixed to the door via a sheet metal pressing 15, having a central web 16 against the door in use and upper and lower flanges 17,18 within plastics material mouldings 19,20. The latter give the impression of being brackets 3,4, although they are in reality covers. Screws 21 passing through the flanges engage in the bores 12 for fastening the extrusion 11 to the pressing.

The door plate 5 is a single moulding extending the height of the handle and having apertures 22 aligned with apertures in the web of the pressing for screws (not shown) to fix the handle to the door. The screws fasten the pressing 15, by acting via the door plate.

The extrusion 11 has a front wall 31, albeit covered with a decorative strip 32. Within the front wall, and adjustably positioned by a grub screw 33, is a static pressure plate 34 for a tubular resilient vessel 35. On the other side of the vessel, there is arranged a moving pressure plate 36, against which the trigger 8 bears. The trigger has lips 37 which pass around the outside of lips 38 of the extrusion 11, thus locating the trigger laterally whilst allowing it to be moved towards the extrusion. Internally of the extrusion, the trigger bears at longitudinal strips 39 against steps 40 on the moving pressure plate. These two parts are adhered and sealed together at the strips/steps, with the strips being interconnected top and bottom by fillets 41 between the strips 39 fitting and sealed to complementary formations on the moving pressure plate. Arrangements for locating the trigger at its ends will be described below.

Internally and along their length, the trigger and the moving pressure plate define a void 42. In its face 43 facing the door plate 5, the trigger plate has an array of apertures 44, each normally closed by a ball 45, the balls being held into seats 46 internally of the apertures by springs 47 bearing against the bottoms of blind sockets 48 in the pressure plate.

Towards the bottom of the pressure plate, it is provided with a hollow boss 51 which communicates with the void 42. It carries a bend 52, which is engaged in the lower end of the tubular vessel 35. Bearing in mind that the upper end of the vessel has a non-return valve 53 to be described in more detail below, it will be appreciated that:
  when the vessel is full of disinfectant gel which has flowed on through the bend 52 and up into the void 42 and
  when the trigger is pulled towards the extrusion 11 of the grip 2, the moving pressure plate squeezes the vessel against the static pressure plate 34, displacing gel. This flows into the void 42 and out at ones of the balls that were urged in against their springs by manual pulling on the handle. Thus disinfecting gel is displaced onto the hand.

The lower end of the trigger and moving pressure plate assembly 36/8 has tangs 54 which engage in a secondary lower moulding 55 on the top side of the lower flange 18, whereas the moulding 20 covers the underside of the flange. These two mouldings are held to the flange by a screw 56. The moulding 55 has a recess 57 in which the tangs engage, restricting the assembly 36/8 from moving freely backwards out of engagement with the extrusion 11. Below the bend 52, the moulding 55 has a drain 58 for allowing any excess gel to run down into the bottom moulding 20, which is dish-shaped to collect it. Periodically, on filling of the reservoir, the screw and the bottom moulding can be removed for cleaning out of any such collected gel.

The upper cover moulding 19 is fitted below the upper flange 17 and restricts the upper end of the assembly 36/8 in similar manner, by engagement of tangs 59 in a recess 60. The top end of the decorative strip 32 engages a lower rim 61 of the cover moulding, with the rim passing on round the extrusion 11 to contain the tangs. Behind the recess 59, the moulding has two bosses 62 into which screws (not shown) pass down through the upper flange 17 to secure the moulding. Also two cruciform spigots 63 of the moulding engage in apertures 64 in the upper flange.

The upper end of the extrusion 11 has an adapter moulding 65 engaged in it. It is captivated by the upper screws 21 passing through it via a lip 66 that engages underneath the flange 17. On its underside, the adapter carries a hollow boss 67 onto which the top end of the resilient vessel 35 fits. On its top side and passing through the flange 17, the adapter has another hollow boss 68, with a central spigot 69.

The reservoir has a smaller depending open boss 71, with two further closed bosses 72, which engage the cruciform spigots 63 extending through the flange 17. With an interference fit, the open boss receives an insert 74, with an outturned lip 75. This captivates an O-ring 76. The latter seals the boss 71 in the boss 68. The insert also loosely captivates a non-return valve ball 77, at a tapered seat 78. When the reservoir is not fitted to the handle, the ball engages the seat 78 and closes the boss 71 against out flow of gel. When the reservoir is fitted, the spigot 69 lifts the ball off the seat 78. The boss 71 has a complementary, oppositely facing seat 79, against which the ball is lifted to act in a non-return valve manner against return flow on gripping of the handle and movement of the trigger into the extrusion 11. Thus the gel in the vessel 35 is displaced out at the trigger. When the trigger is released, the vessel recovers its shape. The balls 45 seal the trigger against ingress of air under action of their springs and the vessel is refilled.

It will be appreciated that the balls are arranged against their seats in a manner such as to prevent egress of gel except when they are pressed in. They are not arranged as non-return valves complementary the non-return valve 53 such that, if the trigger were pressed in without pressure on any of the balls, gel would flow at all the balls.

A top moulding 81, which appears to be a bracket in the same way that mouldings 19, 20 appear to be brackets 3,4, is provided to captivate the reservoir in its use position. It has a rotary latch 82. This and the top end of the door plate have complementary formations 83, 84 for locking the top moulding in position. The moulding has a filler port 85 and a bung 86 for topping up of the reservoir with gel without its removal from the handle.

A final detail is that the reservoir has rear rib 87, which engages in a slot 88 in the door plate for lateral location of the reservoir.

Figure 17:
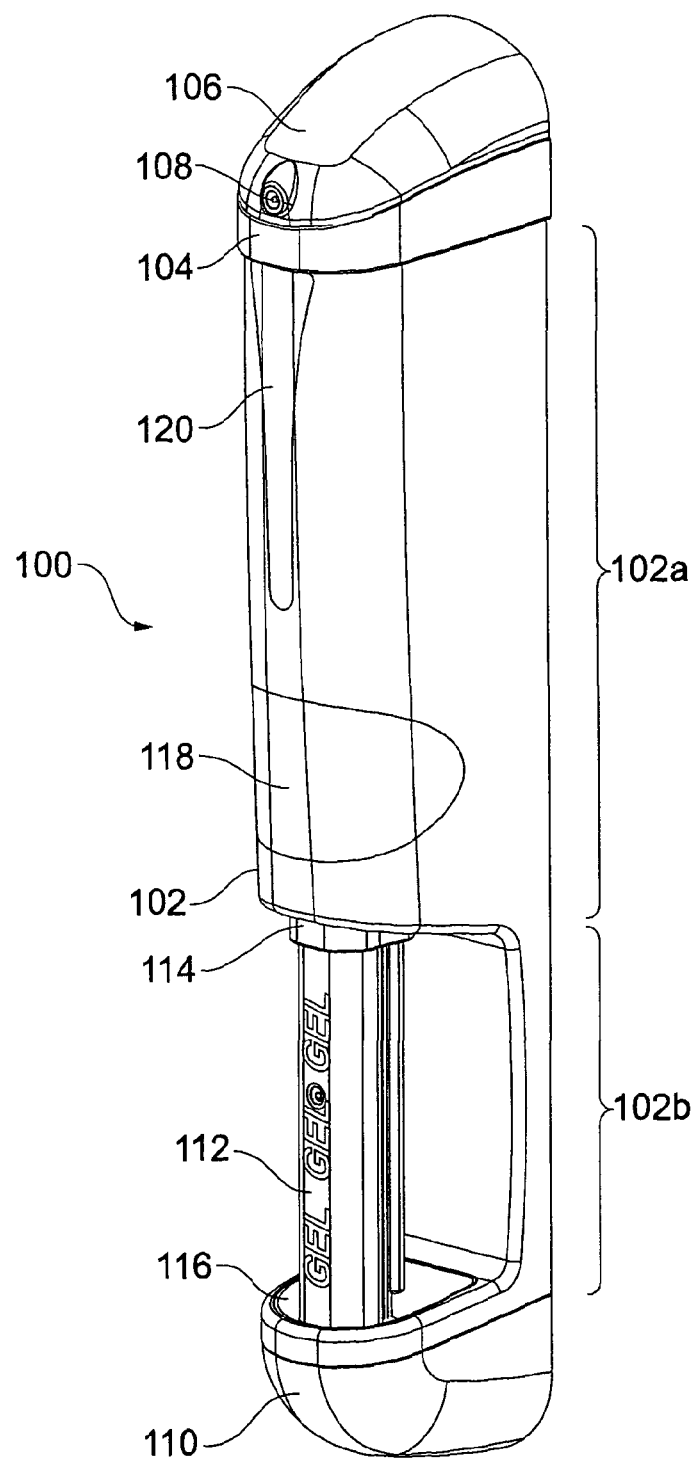
FIG. 17 illustrates schematically a door handle according to a second embodiment of the invention.

FIG. 17 illustrates schematically a door handle 100 according to a second embodiment of the invention. Unless otherwise stated the elements of the door handle are manufactured from thermoplastics (for example Polyethylene or Polypropylene).

The door handle 100 includes a cover 102 that covers elements of the door handle 100. The cover includes an upper portion 102a and lower portion 102b. The upper portion 102a includes a transparent window 118 to allow a level of liquid in an internal reservoir (not shown) to be viewed. The upper portion 102a includes a further transparent window 120 to allow a level of liquid contained in a refill bottle (not shown) to be viewed. The upper portion 102a covers the internal reservoir and the refill bottle. It will be appreciated that the cover 102 may be manufactured from a transparent material, such that individual viewing windows are not required. The cover 102 is generally shaped to provide a cover for the front and sides of the door handle 100. The door handle 100 includes a back plate (not shown) to allow the door handle to be mounted to a door. The cover 102 is removably mounted on the back plate. The lower portion 102b is shaped to allow a user's hand to access a handle portion or first grip 112.

The door handle 100 includes a removable lid 106 mounted on the cover 102 and is manufactured from similar material to the cover 102. The lid 106 includes a locking mechanism 108 that accepts a key. When an appropriate key is inserted and turned in the locking mechanism 108 the lid 106 may be removed. The locking mechanism is of the type typically used for sanitary products such as paper towel dispensers.

The door handle 100 includes a removable bottom cover or base 110. The base 110 is attached to the door handle using an appropriate locking mechanism or suitable attaching means (e.g. a self tapping screw—not shown). The base 110 may be secured using a locking mechanism that allows it to be easily removed. The locking mechanism may be operated using the same key as the lid 106. The base 110 is attached to a portion of the back plate (not shown). The base 110 is removable to allow for construction of the door handle and to allow for further grips to be added to the door handle. Furthermore, the base 110 collects excess liquid from the first grip 112. Therefore, the base 110 is removable to allow for the excess liquid to be removed. A dish-shaped lower member 116 is mounted below the first grip 112 and is shaped to collect excess liquid from the first grip 112, which drains into the base 110.

The first grip 112 is secured to the door handle 100 by a portion of the back plate (not shown) at the lower member 116 and an upper support member 114. The lower member 116 includes an extrusion (not shown), to locate the a proximal end of the first grip 112. The first grip 112 is typically secured to the back plate using self taper screws, for example. The distal end of the first grip 112 extends into a recess shaped to accept the distal end of the first grip 112 of the upper support member 114.

The door handle 100 includes a guard or bumper 104. In this example the guard member 104 is integral to the back plate (not shown) and surrounds a portion of the upper portion 102a of the cover 102. The guard member is arranged to protect the door handle from impact, for example, if a door to which the handle is fitted is opened and brought into contact with an adjacent wall. The guard 104 is constructed from aluminium, but may also be manufactured from high tensile strength plastics (for example Nylon or Polyoxymethylene). The guard 104 may also be constructed from the same material as other elements of the door handle or may be constructed from a different metal or alloy, for example, steel. The guard 104 may be coated with rubber or coloured plastic. The guard 104 is typically arranged such that when the door handle 100 is mounted on a door, the guard 104 extends further from the door than the other elements of the door handle 100. Therefore, if the door is opened such that it makes contact with an adjacent wall, the guard 104 prevents damage to the door handle 100.

Figure 18:
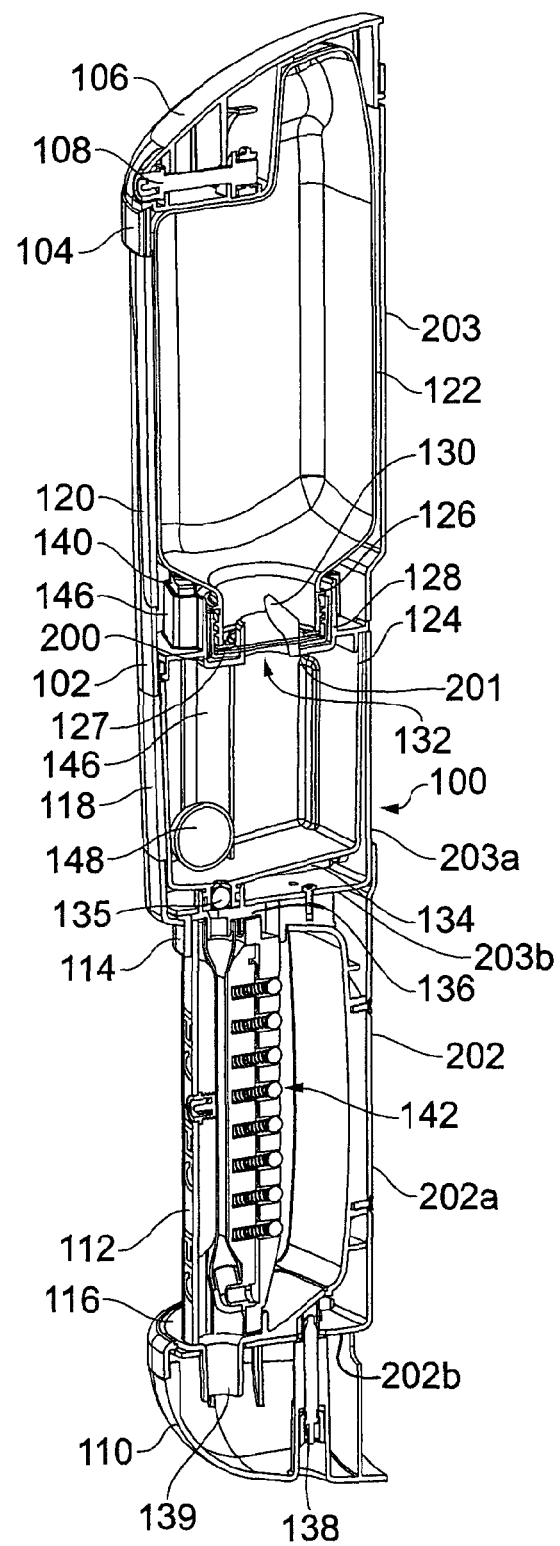
FIG. 18 illustrates schematically a cross section of the door handle shown in FIG. 17.

FIG. 18 illustrates schematically a cross section through the centre of the door handle 100 shown in FIG. 17. Corresponding reference numerals are used in FIG. 17.

Located inside the door handle 100 is a refill bottle or upper reservoir 122. The refill bottle 122 is located in an upper part of the door handle 100 and is arranged in an inverted manner such that an opening 126 in the refill bottle 122 is arranged at the bottom or lower part of the refill bottle. The refill bottle 122 is located in the door handle 100 such that the contents of the refill bottle 122 can be viewed through the viewing window 120. It will be appreciated that the refill bottle 122 may also include an opening at the opposite end of the opening 126 to allow for the refill bottle 122 to be refilled. The opening 126 of the refill bottle 122 includes a seal 127 that is broken when the refill bottle 122 is located in the door handle 100. The neck of the opening 126 also includes a thread such that a removable cap may be fitted when the refill bottle is not located in the door handle 100. In this example, the refill bottle 122 is fitted with an end cap or lid 200 that includes an aperture or outlet 201, such that the refill bottle is placed in the door handle with the lid 200 in place. However, it will be appreciated that the lid 200 having the outlet may be fitted to the refill bottle 122 before it is placed in the door handle 100. When the refill bottle 200 is not in the door handle 100, it may be fitted with a lid having no liquid outlet.

In the door handle 100, a liquid reservoir or lower reservoir 124 is located below the refill bottle 122. The liquid reservoir 124 is located in the door handle 100, such that the contents of the reservoir 124 (e.g. antibacterial or disinfectant liquid or gel) can be viewed through the viewing window 118. The upper part of the liquid reservoir 124 includes a collar 128 to receive the opening 201 of the lid 200 of the refill bottle 122. The collar 128 includes an upstanding piercing element 130, such that when the lid 200 of the refill bottle 122 is located in the collar 128, the piercing element 130 pierces the seal 127 of the refill bottle 122. The piercing element 130 feeds through the opening 131 if the lid 200. The collar 128 also includes an opening 132 to allow liquid from the refill bottle 122 to flow from the opening 126 of the refill bottle 122 into the reservoir 124 under the action of gravity.

In this example above and below are used in reference to the normal orientation of the door handle when it is attached to a door. In the normal orientation of the door handle, the grip is at the lowest part of the door handle. It will be appreciated that the refill bottle may not be mounted above the lower reservoir, rather alongside or below it. If the refill bottle is not mounted above the lower reservoir, pressure may be used to move the liquid from the refill bottle to the lower reservoir. For example, a source of compressed gas may be used.

The lower part of the reservoir 124 includes an opening or aperture 134 to allow liquid to flow from the reservoir 124 into the first grip 112. The opening 134 of the reservoir 124 is in fluid communication with an end cap 136 of the first grip 112.

The opening 134 includes a one-way or non-return valve 135 that allows liquid to flow from the reservoir 124 into the first grip 112, but prevents liquid flow from the first grip 112 to the reservoir 124. However, it will be appreciated that a one-valve is not necessary for operation of the door handle. For example, the lower reservoir 124 and/or the upper reservoir 122 may be pressured using a source of pressurised gas or may include a spring mounted piston. Alternatively, the weight of the liquid in the lower reservoir 124 may be sufficient to prevent liquid flow from the first grip 112 to the reservoir 124.

Adjacent the collar 128 of the liquid reservoir 124, there is located an electrical switch 140, e.g. a micro switch. The switch 140 is connected to a power source (not shown), for example, a button battery. The switch 140 and battery are electrically connected to a light emitting diode (LED) 146 such that when the switch 140 is in an "on" position the LED illuminates the lower reservoir 124. Other light sources may be used and may be provided in a different location to illuminate part or all of the lower and/or upper reservoir. The switch 140 is arranged such that when a refill bottle 122 is located in the door handle 100, the refill bottle 122 applies pressure to the switch 140 and changes the switch to the "on" position. When the refill bottle 122 is removed the switched is changed to an "off" position.

Inside the reservoir 124 there is provided a level indicator ball 148. The ball 148 is designed to be buoyant in the liquid contained in the reservoir 124, such that when the liquid level in the reservoir 124 rises and falls, the ball 148 will typically rise and fall with the level of liquid. The inside of the reservoir 124 is provided with a guide 146 that prevents the ball 148 from moving away from the viewing window 118. The indicator ball 148 allows a user to efficiently check the level of the liquid in the reservoir. This could also be achieved by viewing the level of liquid. Furthermore, the lower reservoir 124 acts as a reserve reservoir, such that when the refill bottle 122 is empty liquid can still be provided by the lower reservoir 124 until the refill bottle is replace or refilled.

In the cross section shown in FIG. 18, an attachment means 138 for the base 110 can be viewed. The attachment means 138 is in the form of a fixing that is inserted through a hole in a back plate 202 and positively engages with the lower member 116 of the door handle 100. An opening 139 is provided in the lower member 116 that allows for liquid from the first grip 112 to drain from the lower member 116 and into the base 110.

An opening 142 can be view in the cross section shown in FIG. 18 which allows a user to grip and apply pressure to the door first grip 112.

In FIG. 18, the back plate of the door handle 100 can be viewed. The back plate includes two separable portions, an upper back plate 203 and a lower back plate 202. It will be appreciated that these may be formed from a single sheet of material. The back plate is manufactured from an alloy or metal, such a aluminium or steel, but may also be manufactured from a high tensile plastics.

The upper back plate 203 is L-shaped, such that a vertical portion 203a is attachable to a door and a horizontal portion 203b provides a support and fixing means for the refill bottle 124, the upper support member 114 and the first grip 112. The guard 104 is also mounted to the vertical portion 203a or may be integral to it. The lower back plate 202 is L-shaped, such that a vertical portion 202a is attachable to a door and the upper back plate 203. A horizontal portion 202b provides a support and fixing means for the first grip 112, the lower dish-shaped member 116 and base 110. Horizontal and vertical are referred to in respect of a door on which the handle is mounted.

Figure 19A:
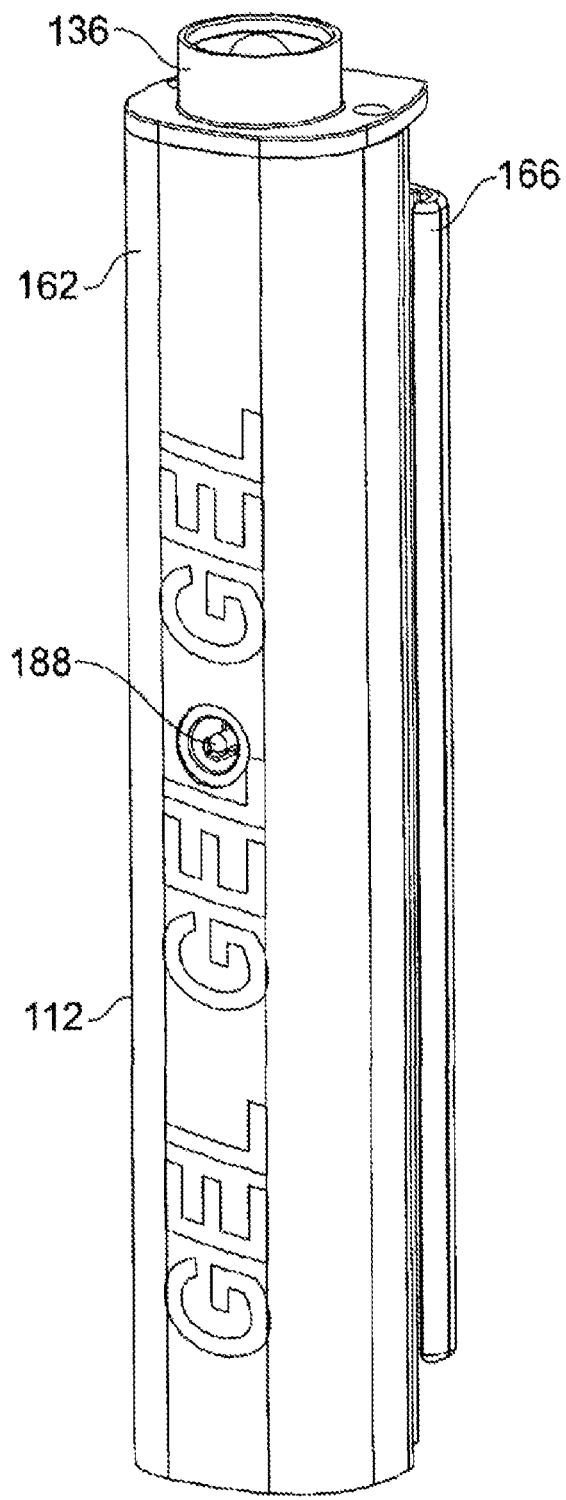
FIG. 19A shows schematically a front-perspective view of a first grip.
Figure 19B:
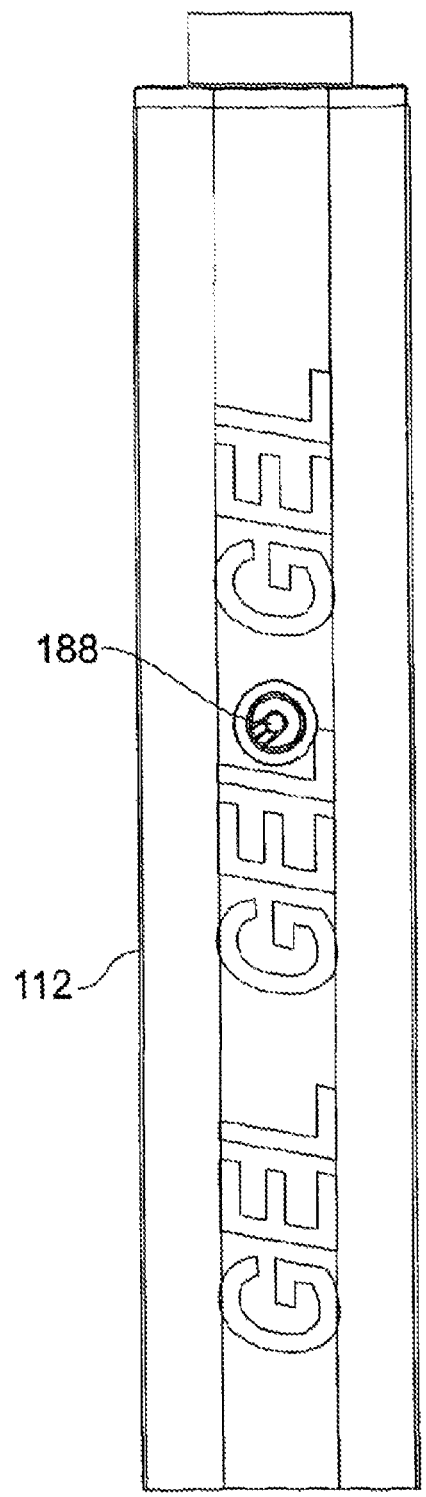
FIG. 19B shows schematically a front view of the first grip of FIG. 19A.

FIG. 19 shows schematically a front-perspective (left) and front (right) view of the first grip 112. The first grip 112 includes a fixed portion 162 and a movable portion 166. The fixed portion 162 is fixed relative to the door handle 100 and typically faces the user. As shown in the figure the fixed portion 162 may include a graphic. The graphic may include a warning message to alert a user that the grip dispenses disinfectant gel or liquid. The movable portion 166 is moveable relative to the door handle 100 and typically faces away from the user. The fixed portion 162 is fixed to the end cap 136. The fixed portion 162 is manufactured from metal or an alloy, for example steel or aluminium. The movable portion 166 is manufactured from a high tensile strength thermoplastic (for example Nylon or Polyoxymethylene). However, the movable portion 166 may also be constructed from the same material as other elements of the door handle or may be constructed from a metal or alloy. The first grip 112 includes a grub screw 188.

Figure 20:
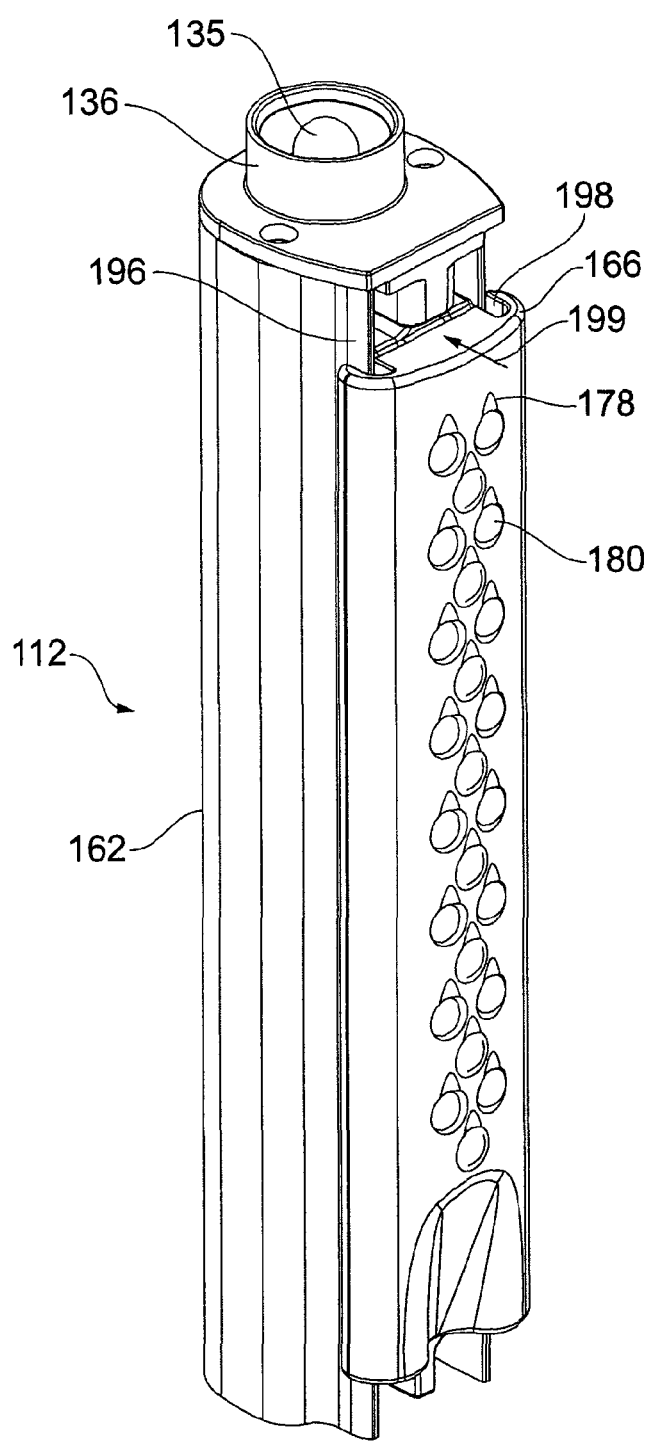
FIG. 20 shows schematically a rear-perspective view of the first grip.

FIG. 20 shows schematically a rear-perspective view of the first grip 112. Corresponding reference numerals are used in FIG. 20 as in FIG. 19.

The rear movable portion 166 is provided with a number of dispensing elements 178 arranged in a regular pattern. Other patterns of holes are envisaged. The dispensing elements 178 are closed with steel balls or spheres 180 which are urged into a closed position. Balls of other materials may be used including plastics or other metals. The diameter of the spheres 180 is greater than the diameter of the opening of the dispensing elements 178 such that the spheres 180 are not urged out of the dispensing element 178. The fixed portion 162 is provided with elongate extrusions 196 which engage with elongate grooves 198 in the movable portion 166 to allow the movable portion 166 to move in the direction of arrow 199 relative to the fixed portion 162. The moveable portion 166 is arranged to form a trigger for dispensing liquid.

Figure 21:
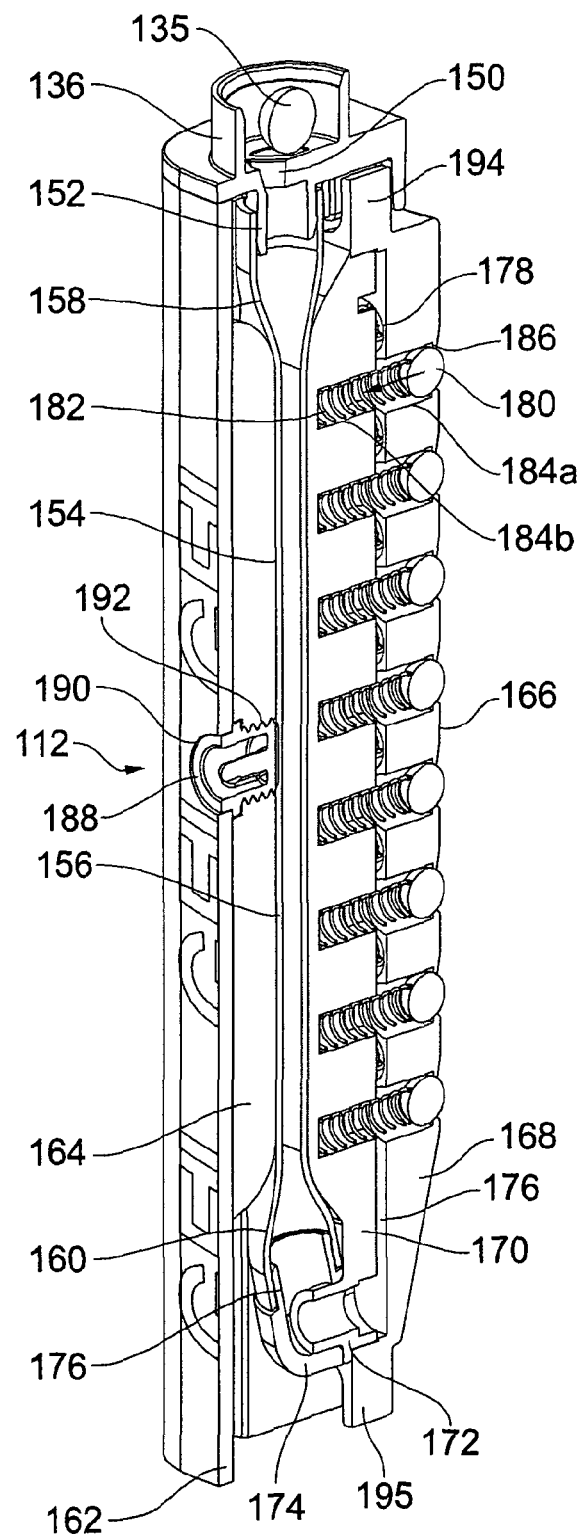
FIG. 21 shows schematically a cross section view of the first grip.

FIG. 21 shows schematically a cross section of the first grip 112 shown in FIGS. 19 and 20. Corresponding reference numerals are used in FIG. 21 as in FIGS. 19 and 20.

In FIG. 21, the end cap 136 includes an aperture 150 which allows liquid to flow into a collar 152. The aperture 150 is closable with the non-return valve 135. Attached to the collar 152 is a flexible elongate tube or tubular resilient vessel 154. The tubular resilient vessel 154 forms a displacement device. The elongate tube 154 includes a liquid inlet 158 coupled to the collar 152 using an interference fit via a lip arranged at the outer periphery of the collar 152, a central region 156 and an outlet 160. The outlet 160 is coupled to a coupling 174 using an interference fit via a lip arranged at the outer periphery of a collar outlet 176. The elongate tube 156 is manufactured from an elastomer (e.g. silicone).

The coupling 174 is coupled to the movable portion 166 via a fluid inlet 172. The moveable portion 166 includes two elements 168, 170. The first element 168 is provided with a plurality of dispensing holes or liquid outlets 184a that run from the external surface to the opposing surface of the first element 168. The diameter of the liquid outlets 184a is 5 mm, but may be varied, for example the liquid outlets 184a may have a diameter in the range from 1 to 10 mm, including 1 mm, 2 mm, 3 mm, 4 mm, 5 mm, 6 mm, 7 mm, 8 mm, 9 mm or 10 mm. The liquid outlets 184a are sized to accommodate the balls 180. The external surface of the first element 168 forms a trigger surface of the first grip 112. At the external surface of the first element 168, each of the liquid outlets 184a is provided with a seat 186. The seat 186 is in the form of a lip having a diameter of 4.5 mm, compared to the diameter of 5 mm of the liquid outlet 184a. It will be appreciated that the diameter of the liquid outlet 184a will be greater than the diameter of balls 180 to allow the balls to move and that the seat 186 will have an internal diameter less than the diameter of the balls 180 to prevent the balls 180 being urged from the trigger 166. The element 168 includes a recess in the surface opposite the external face to provide a liquid channel 176 and to accept a second element 170. The second element 170 includes a plurality of blind holes 184b, which align with the liquid outlets 184a of the first element 168 when the movable portion 166 is assembled. During assembly of the movable portion 166, a spring 182 is arranged in each of the blind holes 184b and the balls 180 are arranged in each of the liquid outlets 184a, such that when the moveable portion 166 is assembled the springs 182 urge the balls 180 against the seat 186, thus providing the dispensing elements or valve mechanisms 178. To provide a channel 176 between the first and second elements 168, 170 of the movable portion 166, the second element 170 is provided with a lip around its periphery edge which abuts with the first element 168. Liquid enters the channel 176 from the liquid inlet 172 arranged in the second element 170. The liquid inlet 172 is coupled to the liquid coupling 174. When pressure is applied to one or more of the balls 180, liquid may flow from one or more of the dispensing elements 178. However, when the balls 180 are urged against the seat 186, egress of liquid from the outlet 184a is prevented.

The first and second elements 168, 170 are held together using bolts and cooperating threads in either the first or second elements 168, 170.

In this example, the spring 182 is a helical spring, but other types of spring or resilient members may be used urge the balls to close the dispensing elements 178.

The movable portion is held in a static position using a tang 194, 195 arranged at opposing ends of the moveable portion. A tang 194 is received in a recess in the cap element 136. A tang 196 is arranged at the opposite end of the movable element to tang 194 that is received by a guide in the lower member 116. The tangs 194, 196 allow the movable portion 166 to move in a direction toward the fixed portion 162, but prevent the movable portion 166 from separating completely from the fixed portion 162

In FIG. 21, there is a fixed pressure plate 164 that is arranged between the elongate tube 154 and the fixed portion 162. The elongate tube 154 being arranged between the fixed pressure plate 164 and the movable portion 166. The fixed pressure plate 164 is movable by rotation of the grub screw 188. The grub screw 188 includes a lip which abuts with a hole 190 in the fixed portion 162. The fixed pressure plate 164 is provided with a cooperating thread 192. When the grub screw is rotated (in a clockwise direction, for example), the grub screw cannot move axially relative to the fixed portion 162. Therefore, the fixed pressure plate 164 is moved away from the fixed portion 162 thus compressing the elongate tube 154, particularly in the central region 156. If the grub screw is rotated in a counter-clockwise direction, the pressure plate 164 is moved toward the fixed portion 162. It will be appreciated that the fixed pressure plate 164 may not be movable with respect to the fixed portion 162 and may be integrally formed with the fixed portion 162.

In operation, the refill bottle 122 is placed in the door handle 100 which fills the lower reservoir 124 with liquid. The liquid flows into the end cap 136 from the liquid reservoir 124 and flows through the elongate member 154 and into the movable element or trigger 166. Since, the end cap 136 is substantially at the same level as the tang 194 (which is at the same height at the upper most dispensing elements 178), the liquid will continue to flow into the recess or channel 176, filling the recess. The liquid that fills the channel 176 will also flow to the dispensing elements 178. Thus the first grip is primed with liquid. When the movable portion 166 is moved toward the fixed portion 162, the central region 156 of the elongate member 154 is compressed against the fixed portion 162 (and the pressure plate 164). Thus liquid in the elongate member 154 flows toward the inlet 158 and the outlet 160. The liquid that flows toward the outlet 160 flows into the channel 170 of the movable portion 166. The liquid that flows toward the inlet 158 (toward the refill reservoir 124) will be prevented from flowing into the reservoir 124 by the non-return valve 135. The movable portion 166 is typically moved using a hand, such that digits will contact one or more of the balls 180. The contacted ball 180 moves away from its respective seat 186 (in the direction indicated on the figure) into the liquid outlet 184a and allows liquid to flow out of the outlet 184a under the action of the trigger 168 being moved toward the fixed portion of the grip 112. When the first grip is released, the elongate member 154 will return to its original (uncompressed) form such that it will be refilled from the lower reservoir 124.

Figure 22:
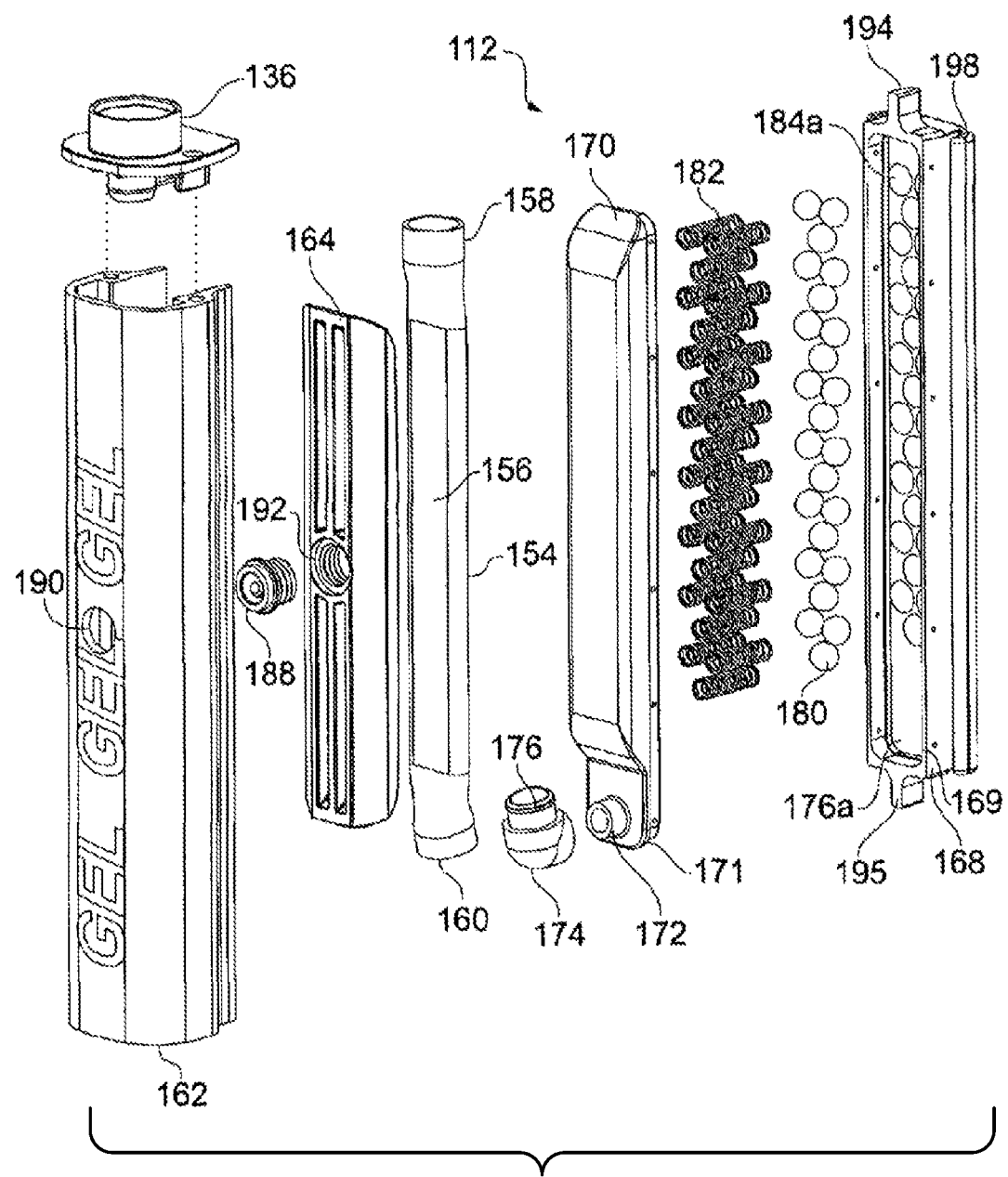
FIG. 22 illustrates schematically the elements of the first grip that are shown in FIG. 21 in an exploded view.

FIG. 22 illustrates schematically the elements of the first grip 112 that are shown in FIG. 21 in an exploded view. Corresponding reference numerals are used in FIG. 22 as in FIG. 21.

In FIG. 22, the cross section of the fixed portion 162 can be seen as being generally U-shaped. A generally U-shaped cross section is used to accommodate the other elements of the first grip 112. A periphery edge 171 of the second element 170 that abuts with a face 169 of the first element 168 is visible in FIG. 22. The recess 176a formed in the first element 168 is shown in FIG. 22 that forms the recess or channel 176 in the trigger 166.

Figure 23:
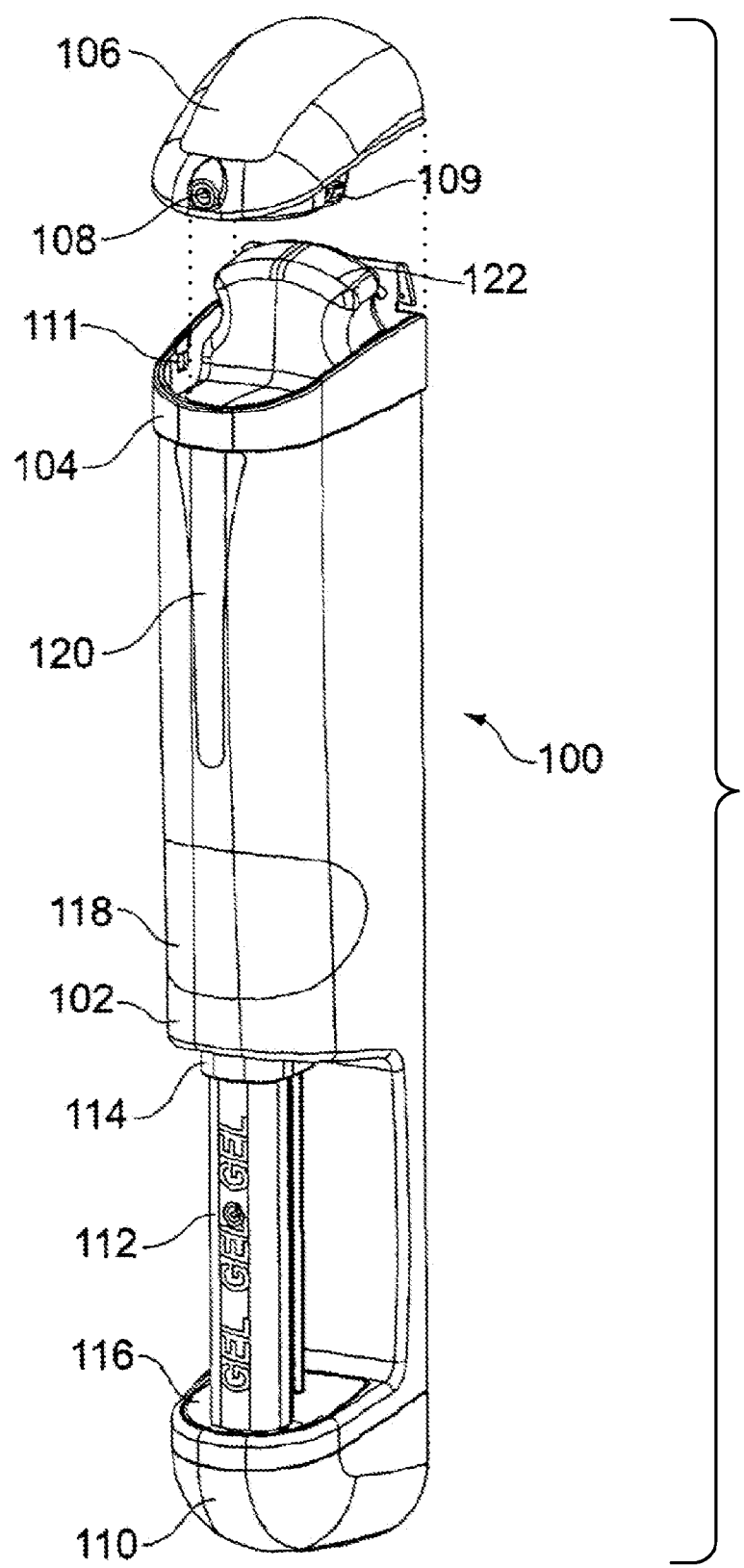
FIG. 23 illustrates the door handle with a lid removed.

FIG. 23 illustrates the door handle 100, with the lid 106 removed. Corresponding reference numerals are used in FIG. 23 as those used in FIGS. 17 and 18.

In FIG. 23, the lid 106 is shown removed to reveal the top of the refill bottle 122. The lid is shown with movable tang 109 that engages with a recess 111 in the cover 102. It will be appreciated that the lid is provided with a tang 109 on opposing sides of the lid 106 and the cover 102 is provided with a recess on opposing sides of the cover 102. The tang 109 is movable to allow the lid 102 to be removed and/or locked into position. The tang 109 is operated by turned the locking mechanism 108 using an appropriate key, for example. The movable tang 109 may be spring loaded such that lid 106 may be pushed into position without the use of a key.

Figure 24:
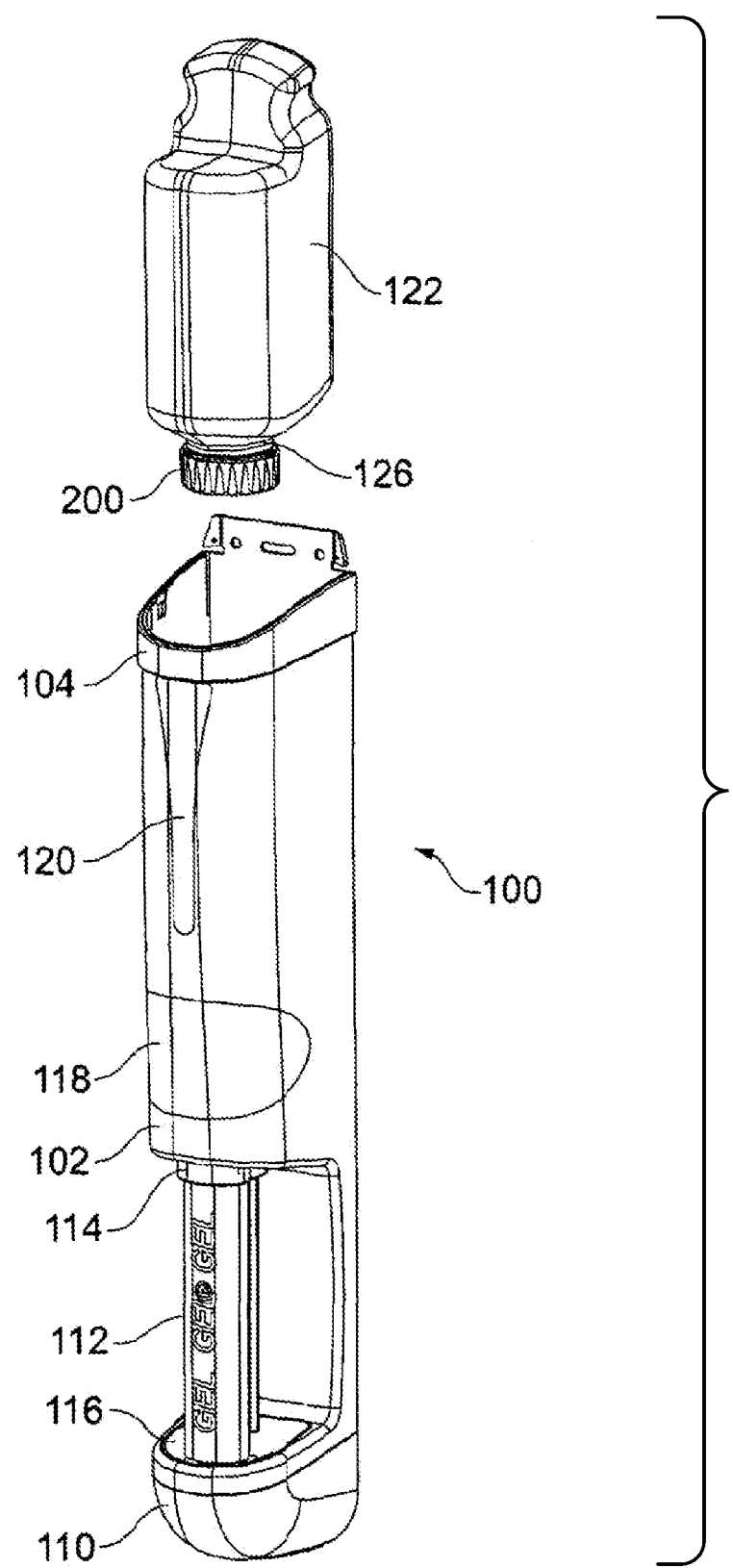
FIG. 24 illustrates schematically the door handle with the lid removed and a refill bottle removed.

FIG. 24 illustrates schematically the door handle 100, with the lid 106 removed and the refill bottle 122 removed. Corresponding reference numerals are used in FIG. 24 as those used in FIGS. 17 and 18. The removal bottle 122 is shown in FIG. 24 is removed from the door handle 100 with the lid 200 arranged at the outlet 126.

Figure 25:
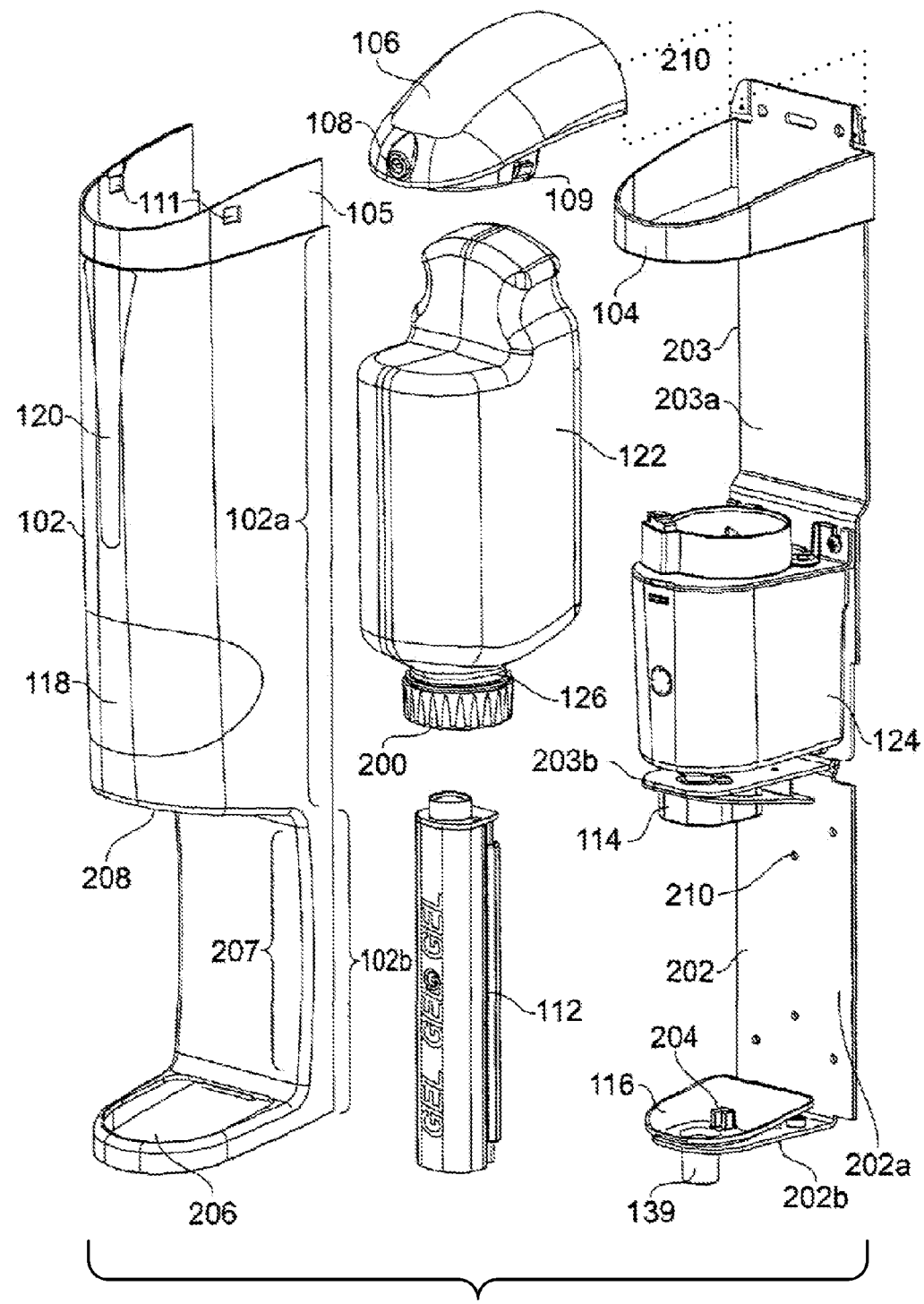
FIG. 25 illustrates schematically the door handle shown in FIG. 17 in an exploded view.

FIG. 25, illustrates schematically the door handle 100 in an exploded view (excluding the base 110). Reference numerals are used in FIG. 25 corresponding to those used in FIGS. 17 to 24.

The cover 102 for the door handle 100 is shown in the figure. The cover 102 is shown having a generally u-shaped upper portion 102a to accommodate elements of the door handle 100. A lower portion of the cover 102b includes a cutaway or recessed area 207 to allow a user to grip the grip 112. In the lower portion of the cover 102b, there is an opening 206 for the lower member 116. There is also provided in the lower portion of the cover 102a an opening 208 to receive the upper support member 114. The upper portion of the cover 102a includes a region 105 that is located within the guard 104, In this example, the region 105 includes a recessed region so that the guard 104 is flush with the surface of the cover 102. However, it will be appreciated that this arrangement is provided for atheistic reasons.

The back plates 202, 203 are provided with fixing holes 210 to allow the door handle to be mounted on the surface of a door.

The lower member 116 is illustrated in the figure with an extrusion 204. The tang 196 (shown in FIG. 21) of the first grip 112 engages with the extrusion 204 to allow the movable portion or trigger 166 (shown in FIG. 21) to move in a direction toward the fixed portion 168 (shown in FIG. 21), but prevent the movable portion 166 from separating completely from the fixed portion 168 of the first grip 112.

Figure 26:
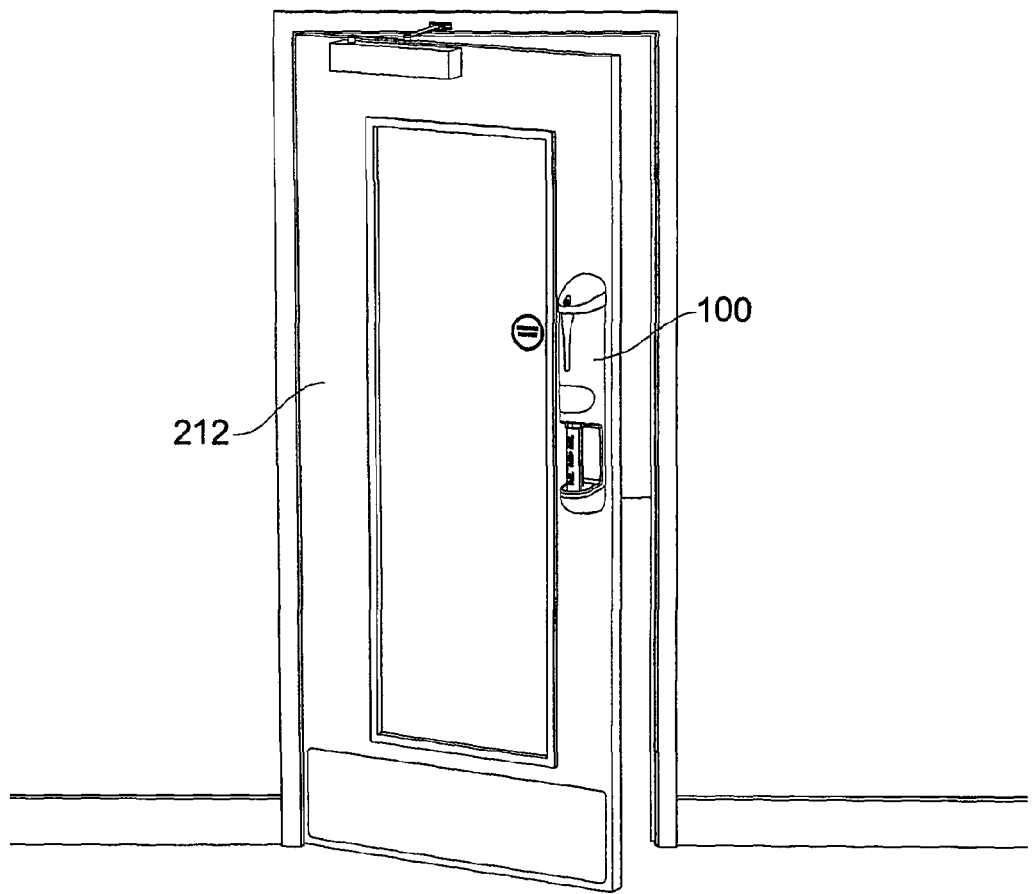
FIG. 26 illustrates the door handle according to the second embodiment of the invention mounted on a door.

FIG. 26 illustrates a door handle 100 according to the second embodiment of the invention mounted on a door 212.

Figure 27:
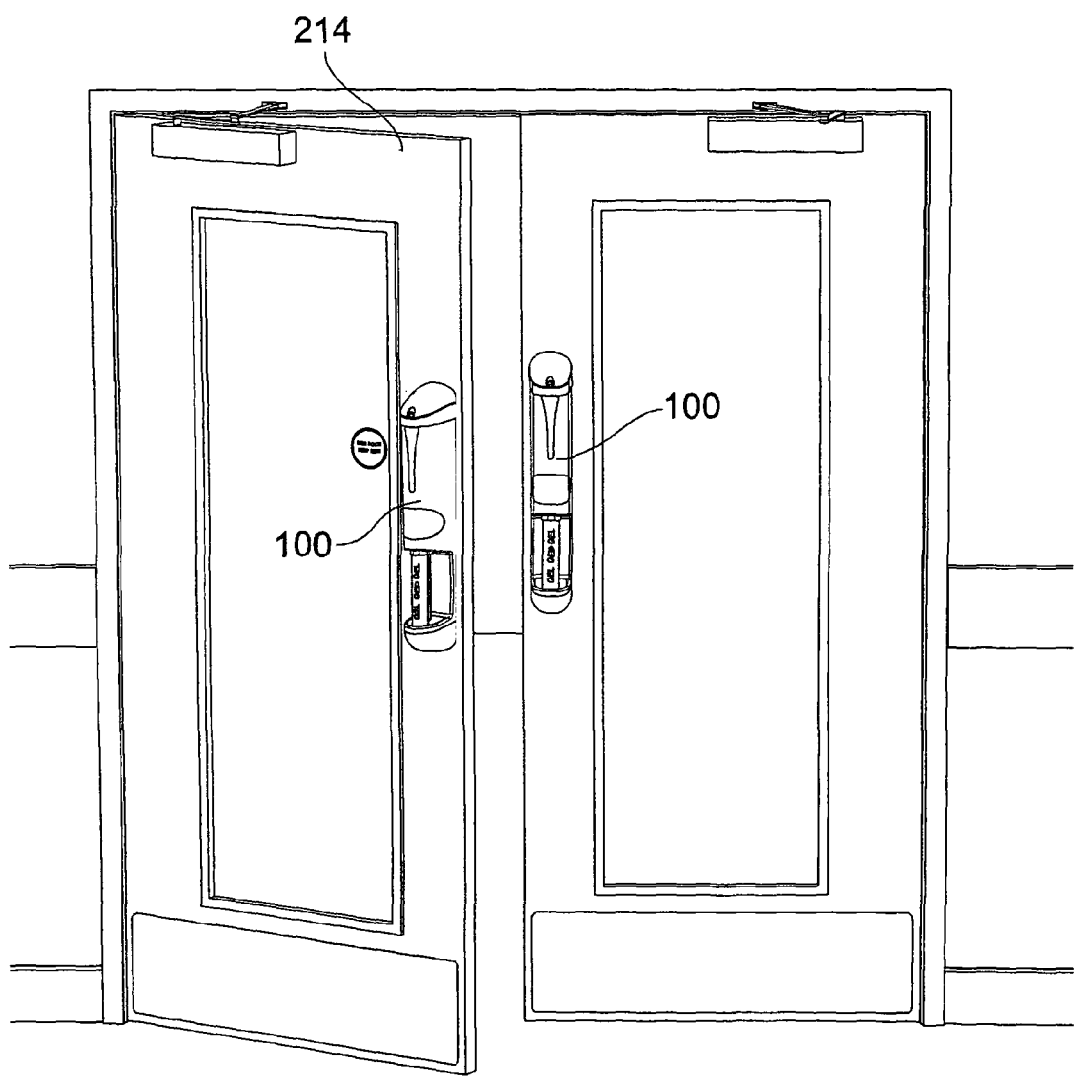
FIG. 27 illustrates a pair of door handles according to the second embodiment of the invention mounted on a pair of doors.

FIG. 27 illustrates two door handles 100 according to the second embodiment of the invention mounted on each leaf of a double door 214.

Figure 28:
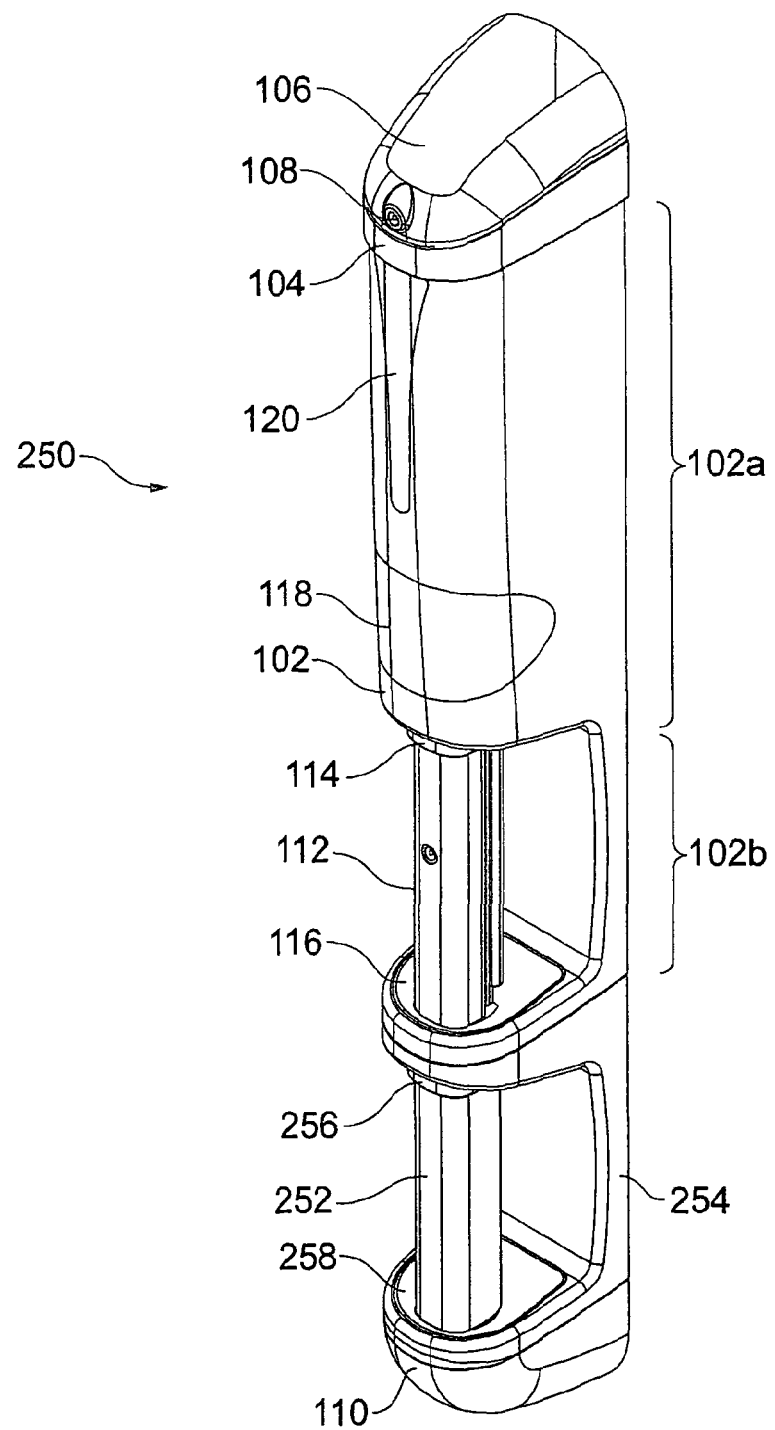
FIG. 28 illustrates schematically a door handle according to a third embodiment of the present invention.

FIG. 28 illustrates schematically a door handle 250 according to a third embodiment of the present invention.

The elements of the door handle 250 that are shared with the door handle 100 have corresponding reference numerals. Unless otherwise stated the elements of door handle 250 are the same as those of door handle 100.

The door handle 250 includes a handle portion or second grip 252. The second grip 250 is arranged in a similar manner to the first grip 112 using an upper support member 256 and a lower member 258. The upper support member 256 includes an aperture for receiving the proximal end of the second grip 252. The distal end of the second grip 252 is located at the lower member 258. The general shape of the second grip 252 is the same as the first grip 112, such that the upper support members 114, 256 have a similar design and the lower members 116, 258 have a similar design.

The door handle 200 includes a cover 254 which has a broadly similar form to the lower portion of the cover 102b. In the figure, the second grip 252, the lower and upper members 256, 258 and the cover 254, are arranged between the lower member 116 and the base 110 such that the base 110 is attached to the a back plate (not shown) of the second grip 252.

Figure 29:
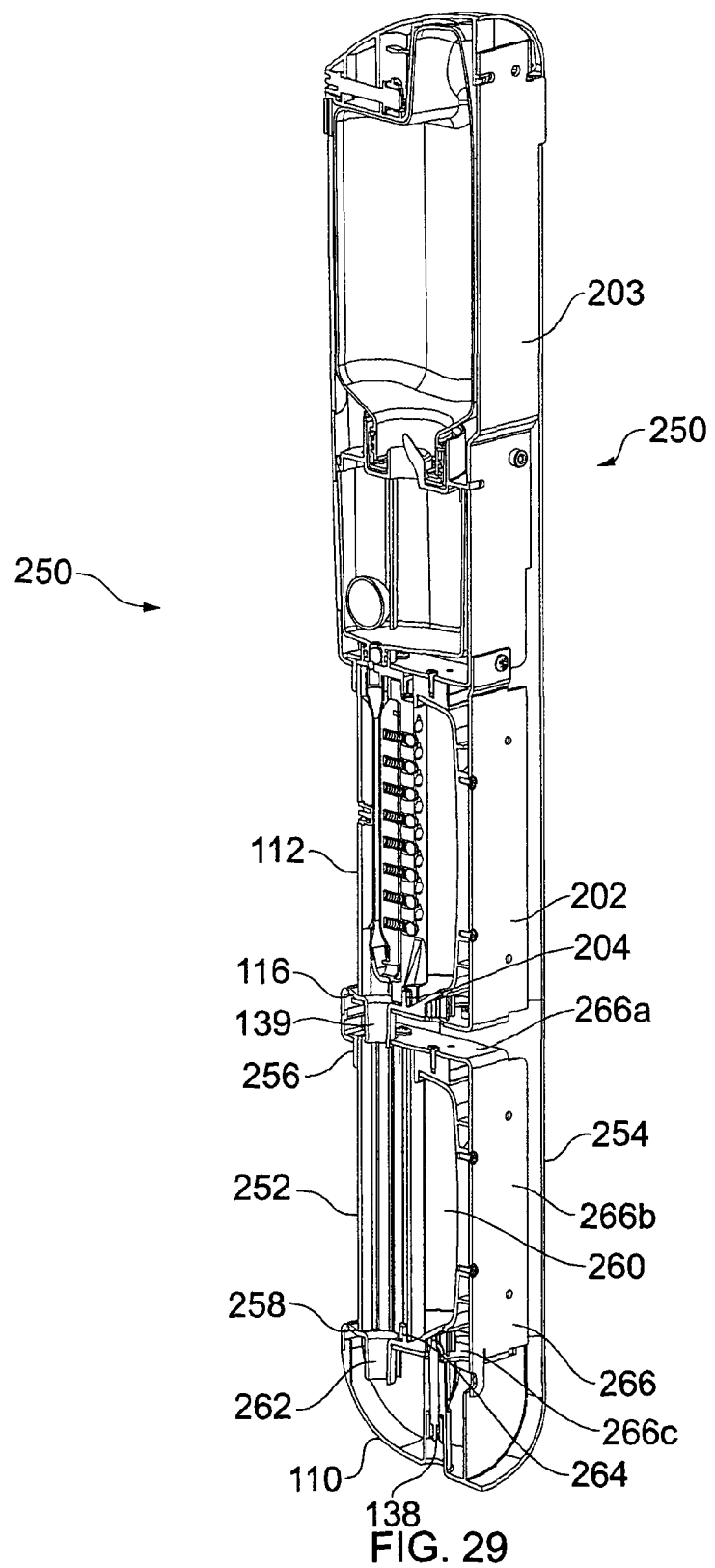
FIG. 29 illustrates schematically a cross section of the door handle shown in FIG. 28.

FIG. 29 illustrates schematically a cross section through the door handle 250.

In FIG. 29 there is provided a c-shaped back plate 266. The back plate is manufactured from a similar material as the back plates 202 and 203. The lower member 258 is attached to a lower horizontal portion of the back plate 266c. The upper support member 256 is attached to an upper horizontal portion of the back plate 266a. The cover 254 is mounted on a vertical portion of the back plate 266b. The cover 254 includes a cutaway region 260 to allow a user access to the second grip 252.

The cover 254 and the back plate 266 are mountable on the surface of a door using a fixing means (e.g., a screw) that is threaded through holes in the cover 254 and the back plate 266. The back plates 202, 203, 266 may be formed from a single piece of material.

The base 110 is attached to the lower horizontal portion of the back plate 266c using the attachment means 138. The lower support member 258 includes an extrusion 246 (similar to extrusion 204) which is received by an aperture in the second grip 252. The second grip 252 is attached to the back plate 266 at the lower and upper horizontal portions 266a, 266b using a fixing means, for example a self taping screw.

The second grip 252 has a general cylindrical form with open ends. Excess liquid that is caught in the lower member 116 that flows into the opening 139 continues to flow through the second grip 252 such that it flows through an opening 262 in the lower member 258 and into the base 110. Therefore, as in the embodiment shown in FIG. 17, the base 110 can be removed for removal of excess liquid.

The second grip 252 is manufactured from aluminium and is coated with an antibacterial coating. The antibacterial coating may be a titanium dioxide based nano-technology photocatalyst which destroys bacteria, spores, viruses, mould, odours and pollutants. For example, the coating may be Toachclean™ or Bioclock™. The grip provides a physical antibacterial action in that the organic compounds on the surface of the grip are minimised. This is in contrast to the first grip 112 that provides a chemical antibacterial action by way of dispensing a liquid or gel.

Alternatively, the second grip 252 may be manufactured from a composite including a high tensile plastics and an antibacterial material (e.g. Microban™) to inhibit the growth of bacteria and mould. Alternatively, the second grip 252 may be manufactured from copper.

The door handle may be provided with an ultra violet (UV) light source that illuminates a surface of the second grip 252 to sterilize the surface of the second grip 252. For example, a commercially available low-pressure mercury-vapour lamp that emits light at 254 nm may be used. Therefore, the second grip does not require an antibacterial coating and can be manufactured from aluminium, for example.

The second grip is shown in arranged below the first grip. However, other configurations are envisaged such as side by side or the first grip below the second grip. The first and second grips are shown vertically arranged, but may also be horizontally arranged on the door.

Figure 30:
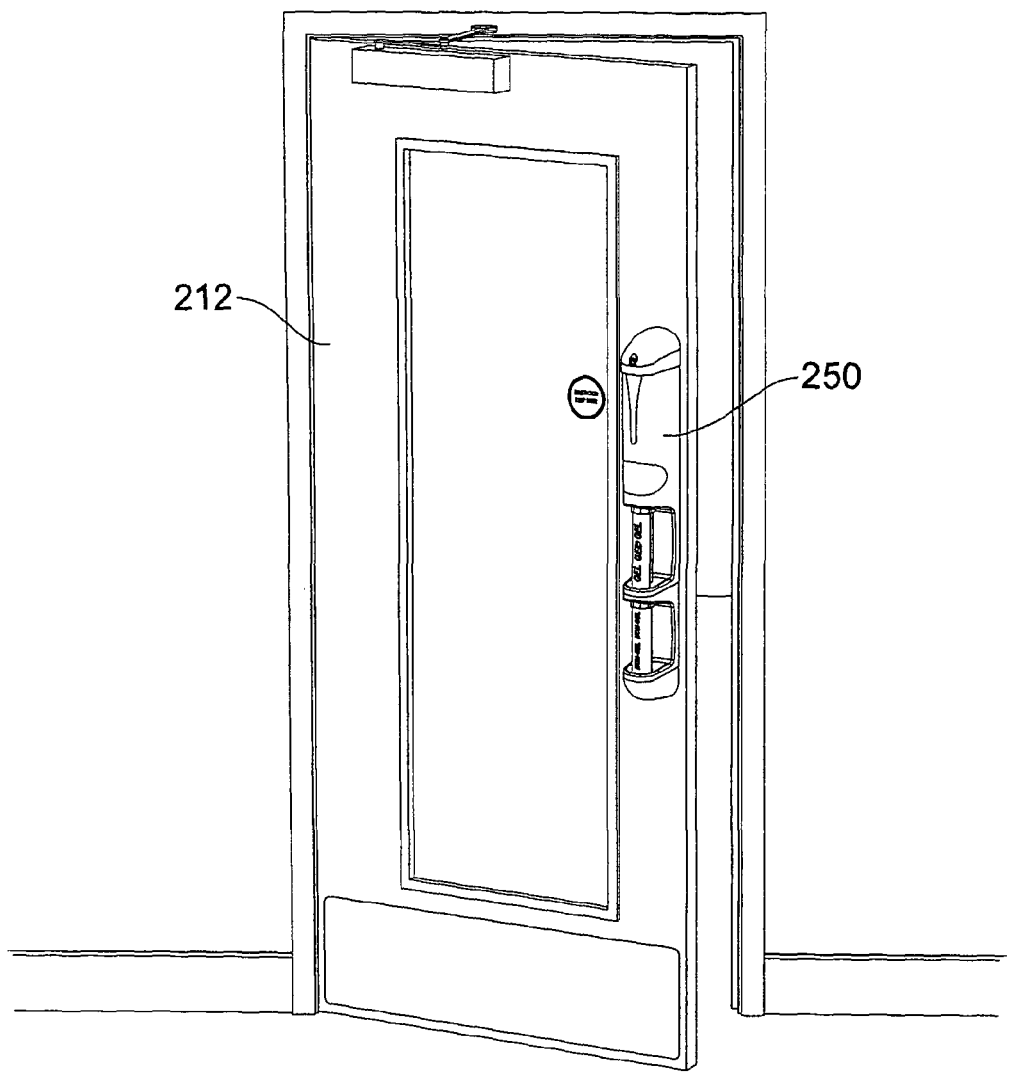
FIG. 30 illustrates the door handle according to the third embodiment of the invention mounted on a door.

FIG. 30 illustrates the door handle 250 according to the third embodiment of the invention mounted on a door 212.

Figure 31:
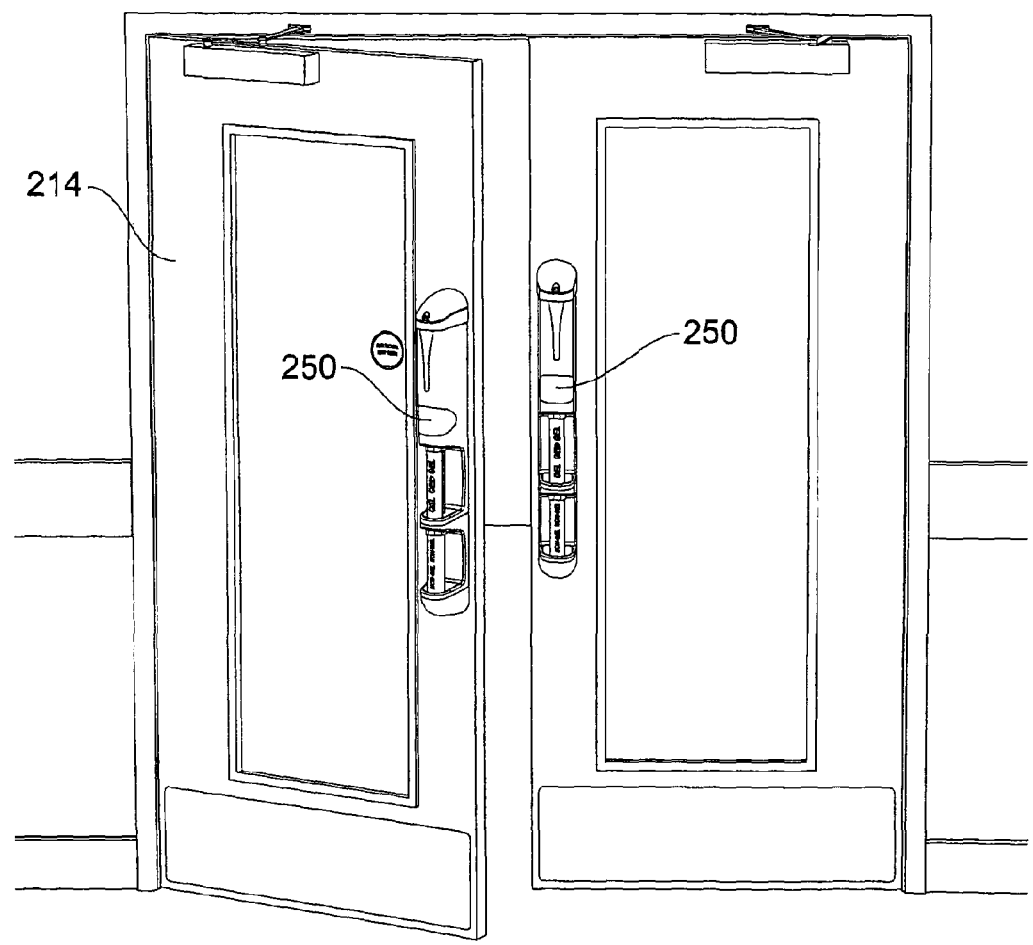
FIG. 31 illustrates a pair of door handles according to the third embodiment of the invention mounted on a pair of doors.

FIG. 31 illustrates two door handles 250 according to the third embodiment of the invention mounted on each leaf of a double door 214.

Figure 32:
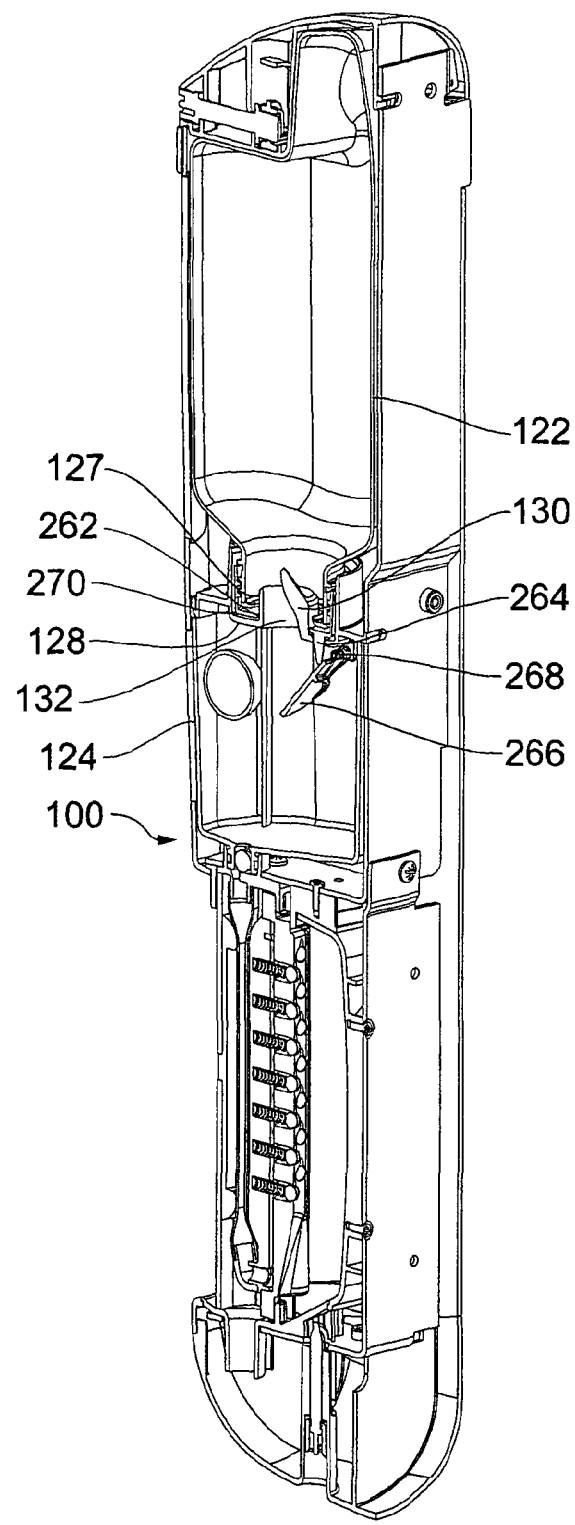
FIG. 32 illustrates schematically a cross section through the door handle 100 shown in FIG. 18 according to a fourth embodiment of the invention.

FIG. 32 illustrates schematically a cross section through a door handle 100 according to a fourth embodiment. The door handle is the same as that of the second embodiment except for the following differences. In FIG. 32, the opening 132 is provided with a flap 266 that is pivotably mounted adjacent the opening 132 on the collar 128. The flap 266 includes a coiled or helical spring 268 that urges the flap 266 closed when there is nothing acting against it. When the flap 266 is the closed position, it closes the opening 132 to prevent contaminates and debris entering the reservoir 124. An upper portion of the reservoir 124 includes a vent (not shown) that allows air to exit the reservoir 124 as liquid enters via the opening 126. The vent is also closed by the flap 266 when it is in the closed position.

The flap 266 is moved from the closed position to an open position by a filament 264 that extends from an end cap 270 fitted to the opening 126 of the upper reservoir or refill bottle 122. The end cap 270 includes an opening 262 to allow liquid to exit and to allow the piercing element 130 to pierce the seal 127. When the refill bottle 122 is placed in the door handle 100, the filament 264 will act against the flap 266 and move it into the open position. When the refill bottle 122 is removed the flap 266 will move to the closed poison under the action of the spring 268.

Figure 33:
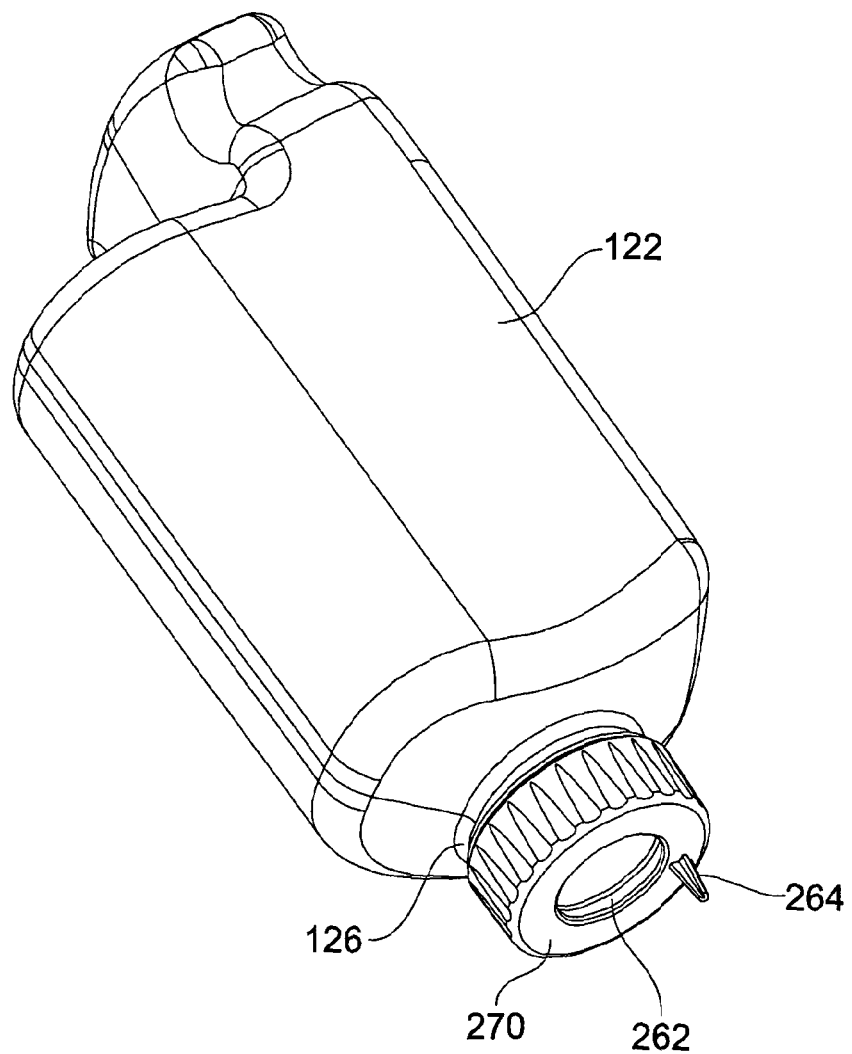
FIG. 33 illustrates the refill bottle for the fourth embodiment of the invention.

FIG. 33 illustrates the refill bottle or upper reservoir 122 according to the fourth embodiment of the invention. In the figure the refill bottle 122 is provided with an end cap 270 which includes the filament 264 and the opening 262 to expose the seal (not show). It will appreciated that the reservoir may be supplied with a regular end cap (for example one without the opening or the filament) and the end cap is replaced for the one shown in the figure before installing it in the handle.

It will be appreciated that the flap arrangement shown in FIG. 32 may also be applied to modify the twin grip door handle of the third embodiment shown in FIG. 28.

Several variations suitable for any of the above embodiments are now discussed.

An antibacterial or disinfectant from the upper and lower reservoirs is dispensed from the first grip in the form of a liquid or gel.

The closure of the liquid outlets in the trigger may be provided with leaf springs in the form of tabs bent from a single strip that urge a ball or other complimentary shaped device into the outlet. For example, the liquid outlets may be closed by a hemispherical solid that is urged in the outlet. Alternatively, the closure of the liquid outlets in the trigger may be provided with individual closure members including integrally moulded resilient fingers, which urge their closure members into the liquid outlets. It will be appreciated that the grip may not be provided with closure members.

The flexible elongate tube may be replaced with multiple pumps each in liquid communication with the reservoir. The pump may be a compressible vessel that is disposed between the fixed and movable (trigger) portion of the first grip. Each of the individual pumps may be provide with a liquid outlet that is coupled an outlet in the grip. When the handle is gripped the movable portion compresses each of the pumps against the fixed portion such that liquid is dispensing from the pump's respective outlet onto a surface of the grip.

The liquid may be dispensed from the first grip using a piston and cylinder device mounted with the first grip. Alternatively, liquid may be dispensed from the first grip using a diaphragm and chamber device mounted within the first grip. The first grip may be provided with a return spring to return the trigger after it has been gripped.

REFERENCES

1. WO 2008/153711 A1
2. DE10014472 A1
3. EP1164235 A3
4. GB2421897 A
5. FR2824096 A1
6. US2006/0245818 A1
7. GB2436284 A
8. DE202004006845

The invention claimed is:

1. A door handle adapted to apply liquid or gel (liquid/gel) to a user's hand, the handle comprising:
   a handle grip;
   a liquid/gel reservoir associated with the handle;
   a liquid/gel displacement device in the grip; and
   a hollow trigger displaceably mounted on the grip and adapted to actuate the displacement device when the handle is gripped for displacement of liquid/gel from the device, into the trigger and thence on to a hand or its digits gripping the trigger;
   wherein the trigger is provided with a plurality of liquid/gel outlets which are normally closed and are individually opened by digital pressure on them, whereby the liquid or gel is expelled selectively where the digits act against the trigger.

2. The door handle of claim 1, wherein the reservoir is above the grip with gravity assisting or causing the liquid/gel to flow down.

3. The door handle of claim 1, wherein individual closure members, such as balls, are provided to close individual outlets, with each closure member being urged into its outlet by a respective spring.

4. The door handle of claim 3, wherein the springs are coil springs or leaf springs in the form of tabs bent from a single strip.

5. The door handle of claim 1, wherein closure members are provided to close individual outlets, the closure members being integrally moulded to resilient fingers, which urge their closure members into the outlets.

6. The door handle of claim 1, comprising a non-return valve allowing liquid/gel flow to from the reservoir to the displacement device.

7. The door handle of claim 1, comprising a second grip adapted to provide a physical antibacterial action.

8. The door handle of claim 1, comprising a guard member arranged to protect the reservoir from impact, if a door on which the handle is adapted to be mounted is opened and brought into contact with an adjacent wall.

9. The door handle of claim 1, comprising a second, upper liquid/gel reservoir removably mounted on the handle which, when fitted, is in fluid communication with the liquid/gel reservoir of claim 1 by virtue of an aperture of the upper liquid/gel reservoir engaging with an aperture of the lower liquid/gel reservoir.

10. A door to which is fitted a door handle according to claim 1.

* * * * *